(12) United States Patent
Margalit et al.

(10) Patent No.: US 7,145,660 B2
(45) Date of Patent: Dec. 5, 2006

(54) MICRO-RESONATOR BASED OPTICAL SENSOR

(75) Inventors: Moti Margalit, Zichron Yaakov (IL); Eyal Berkowicz, Haifa (IL)

(73) Assignee: Lambda Crossing, Ltd., Tel Aviv (IL)

( * ) Notice: Subject to any disclaimer, the term of this patent is extended or adjusted under 35 U.S.C. 154(b) by 217 days.

(21) Appl. No.: 10/868,776

(22) Filed: Jun. 17, 2004

(65) Prior Publication Data

US 2005/0035278 A1    Feb. 17, 2005

Related U.S. Application Data

(60) Provisional application No. 60/494,570, filed on Aug. 13, 2003.

(51) Int. Cl.
G01C 19/72 (2006.01)
G01B 9/02 (2006.01)

(52) U.S. Cl. ...................... 356/477; 356/477
(58) Field of Classification Search ........ 356/459–461, 356/477, 480; 250/227.19, 227.27; 385/12; 372/94

See application file for complete search history.

(56) References Cited

U.S. PATENT DOCUMENTS

| | | | |
|---|---|---|---|
| 4,475,812 A | 10/1984 | Buczek et al. | |
| 4,589,285 A * | 5/1986 | Savit | 73/655 |
| 4,775,214 A | 10/1988 | Johnson | |
| 5,022,760 A * | 6/1991 | Lawrence et al. | 356/461 |
| 5,327,215 A | 7/1994 | Bernard et al. | |
| 5,663,790 A * | 9/1997 | Ekstrom et al. | 356/481 |
| 6,052,495 A | 4/2000 | Little et al. | |
| 6,278,811 B1 | 8/2001 | Hay et al. | |
| 6,504,971 B1 * | 1/2003 | Margalit et al. | 385/24 |
| 6,515,749 B1 | 2/2003 | Pipino | |
| 6,721,053 B1 * | 4/2004 | Maseeh | 385/12 |

FOREIGN PATENT DOCUMENTS

| | | |
|---|---|---|
| EP | 383587 A1 | 8/1990 |
| EP | 383587 B1 | 11/1992 |
| WO | WO 94/00736 | 1/1994 |

OTHER PUBLICATIONS

Single-Mode optical-fiber double-ring resonator with a planar 3×3 fiber coupler, Ja, Optical Letters, Sep. 1993, pp. 1502-1504.*

(Continued)

Primary Examiner—Gregory J. Toatley, Jr.
Assistant Examiner—Patrick Connolly
(74) Attorney, Agent, or Firm—Simon Kahn

(57) ABSTRACT

An optical sensor system for providing an output signal in response to a sensed parameter is disclosed. The sensor system comprises an optical signal source generating an input signal, a sensing element in optical communication with the optical signal source and a detector in optical communication with the sensing element. The sensing element comprises at least two resonant cavity loops exhibiting a common resonant frequency near at least one frequency of the input signal, at least one of the resonant cavity loops being exposed to an external parameter. The external parameter modifies the resonant frequency of the at least one exposed resonant cavity loop thereby modifying an optical output signal. The detector detects any modification in the output optical signal in response to the sensed parameter.

9 Claims, 11 Drawing Sheets

OTHER PUBLICATIONS

Little, Chu, Haus, Foresi and Laine; "Microring Resonator Channel Dropping Filters"—J. of Lightwave Technology, vol. 15, No. 6 Jun. 1997 pp. 998-1005.

Oda, Takat and Toba; "A Wide FSR Waveguide Double Ring Resonator for Optical FDM Transmission Systems"—J. of Lightwave Technology, vol. 9, No. 6 pp. 728-736.

Monovoukas, Swiecki and Maseeh; "Integrated Optical Gyroscopes Offering Low Cost, Small Size and Vibration Immunity"—IntelliSense Corporation—Wilmington, MA.

OW 2400c—data sheet—"Coated Optical Waveguide Grating Coupler Sensor Chip"; MicroVacuum Ltd., Budapest, Hungary.

* cited by examiner

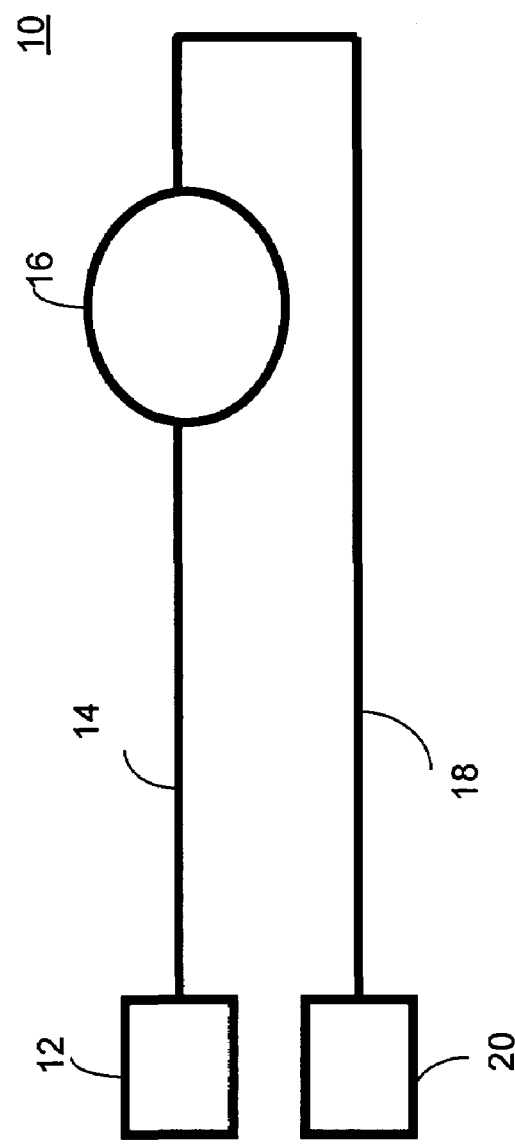
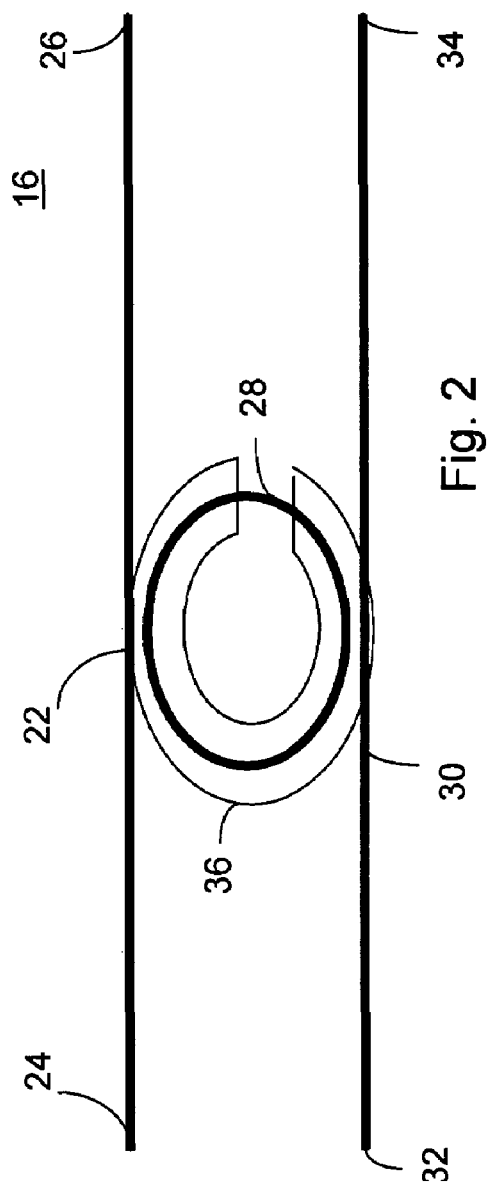

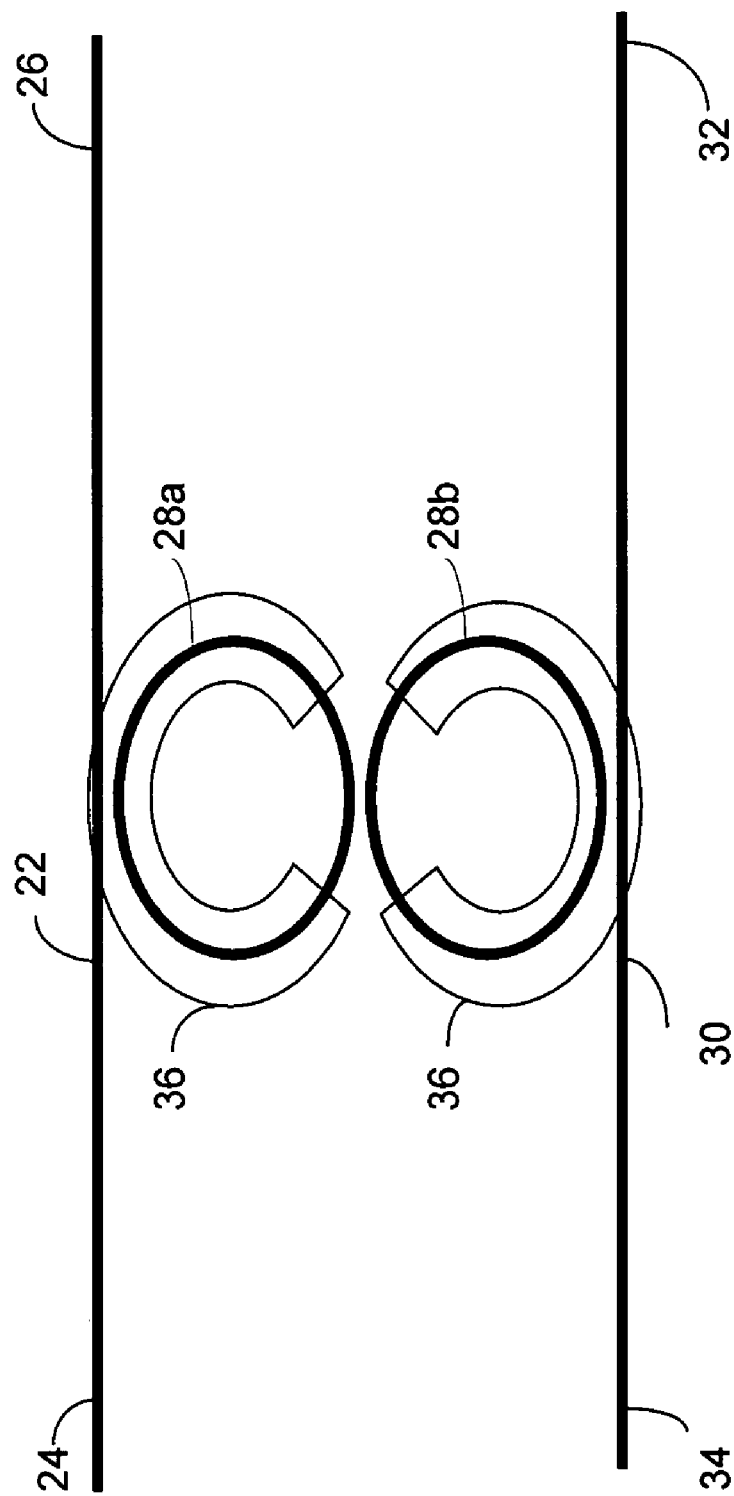

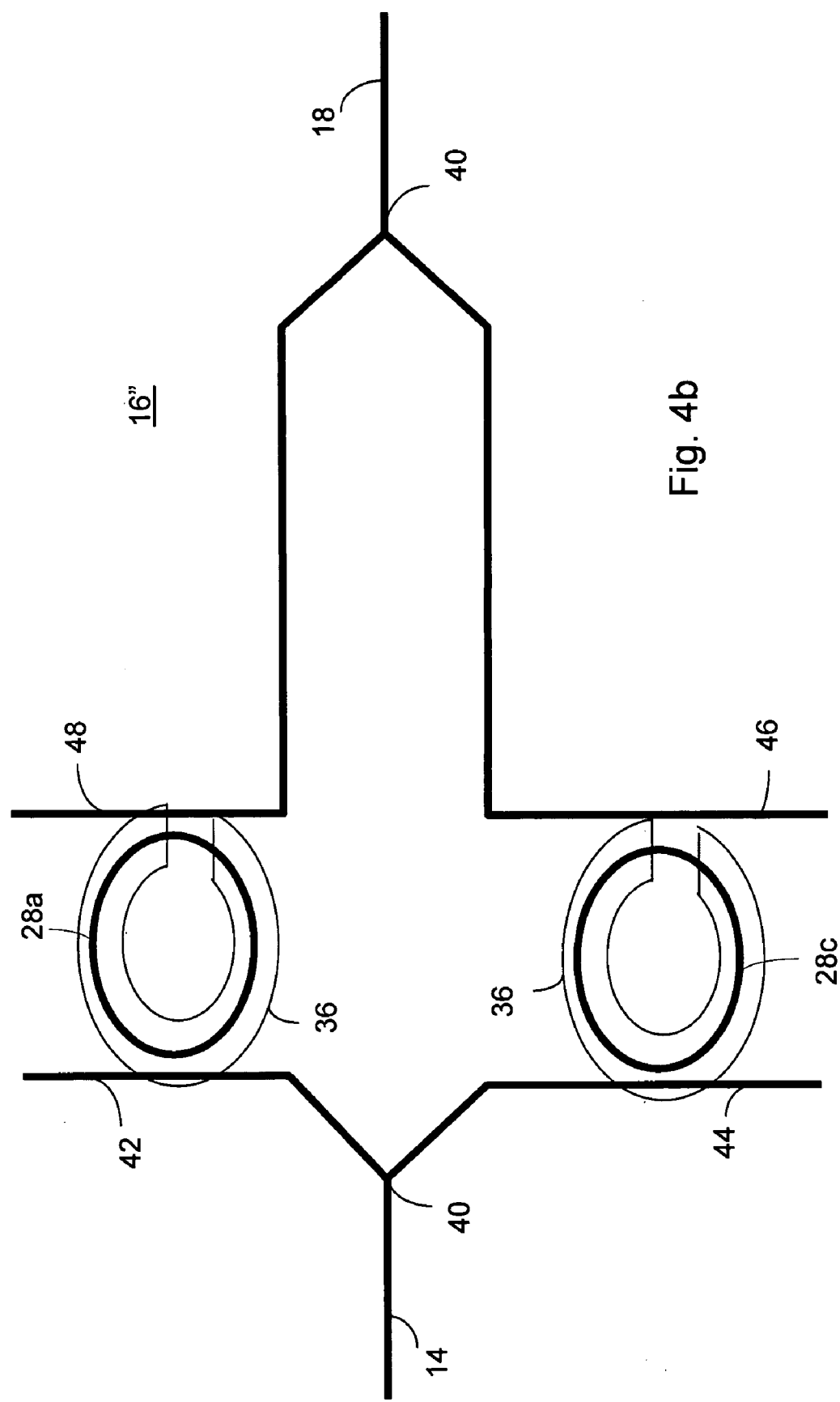

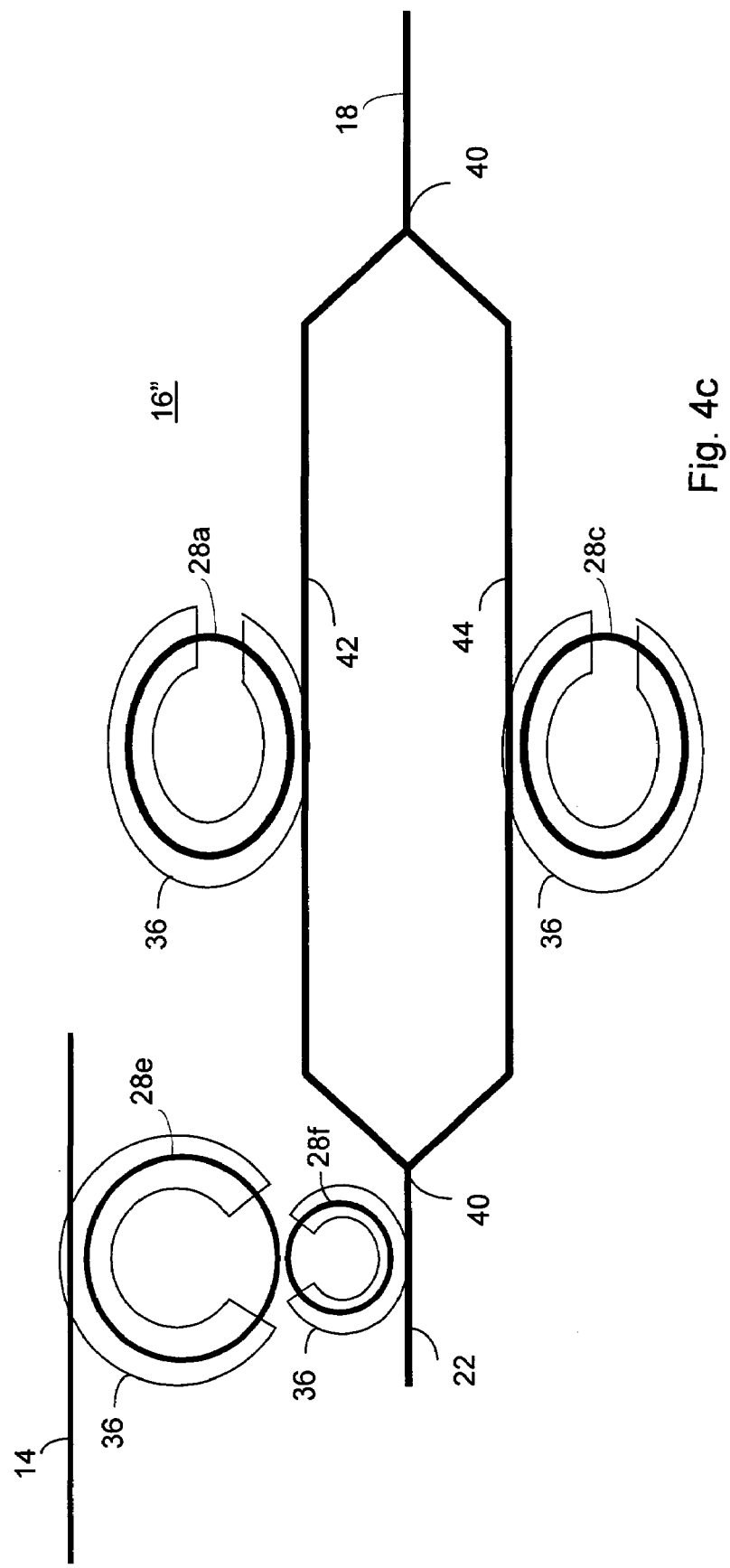

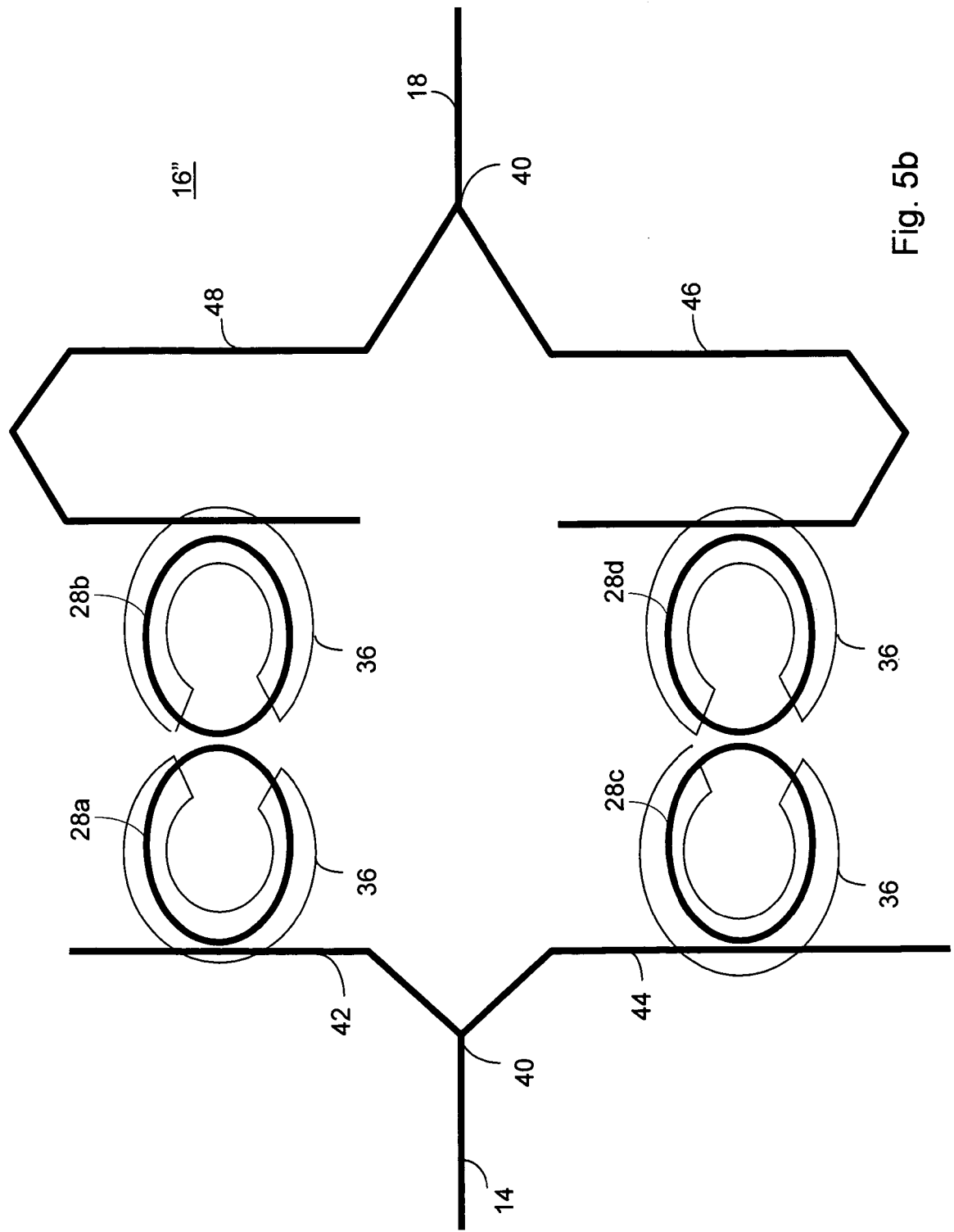

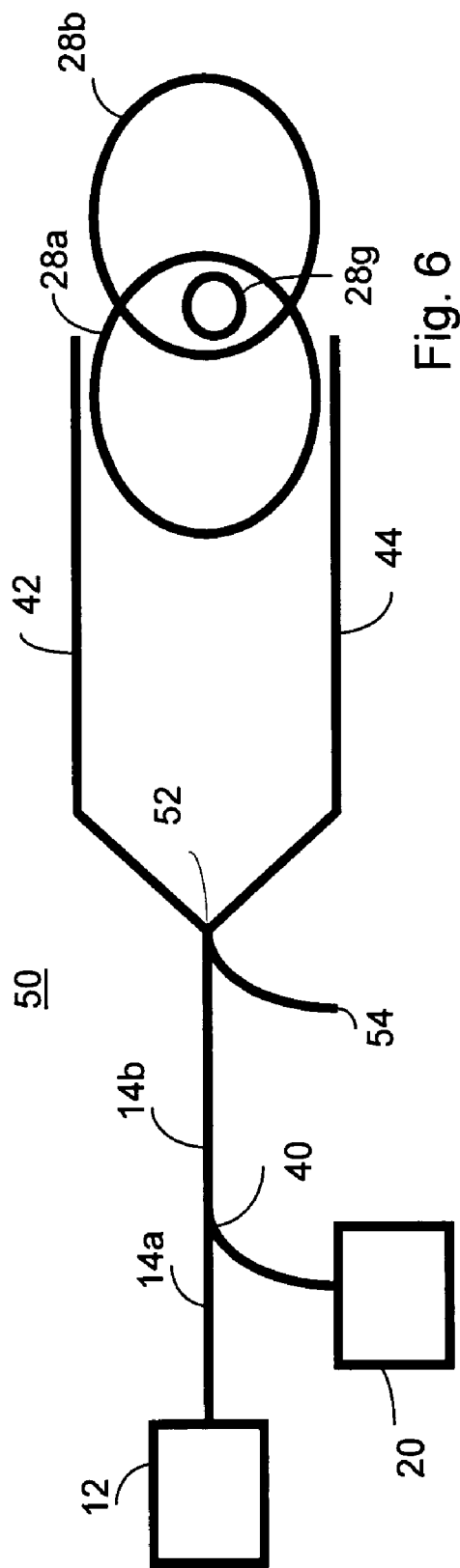
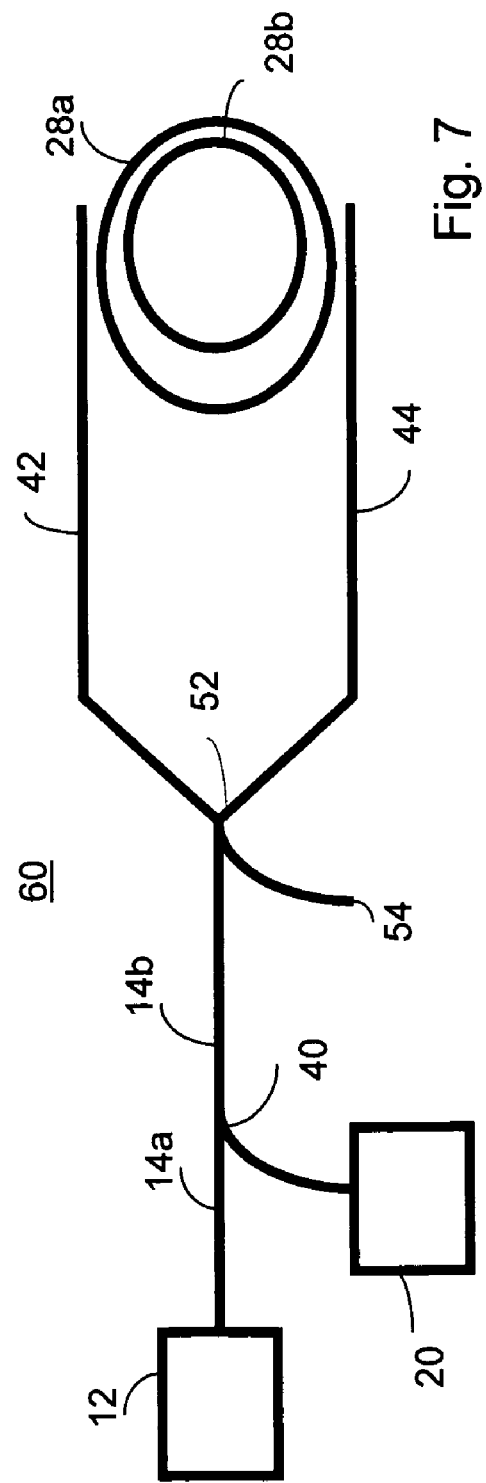

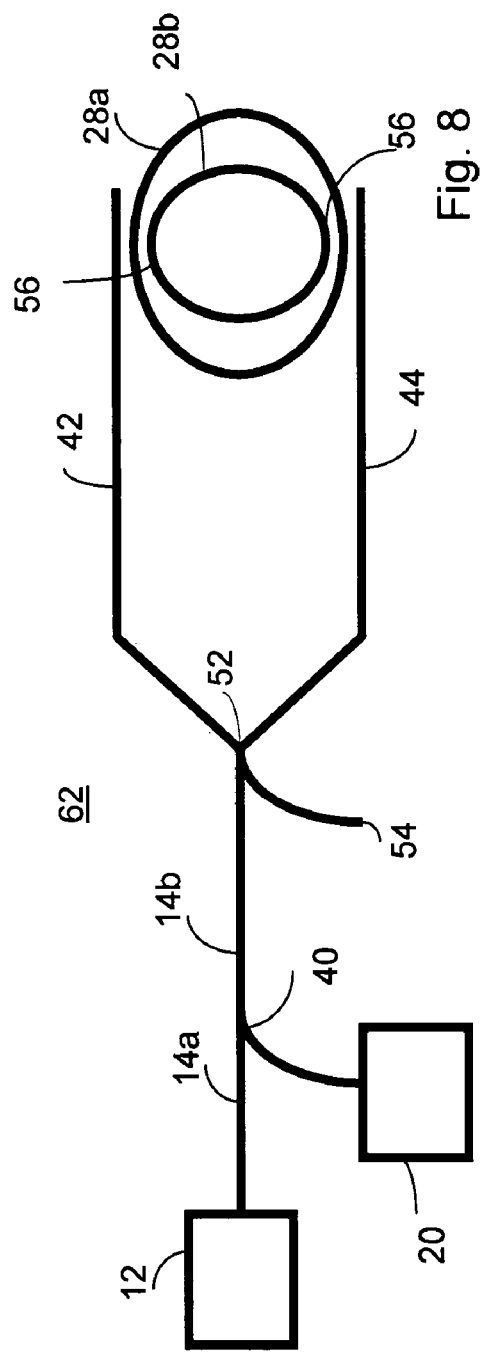
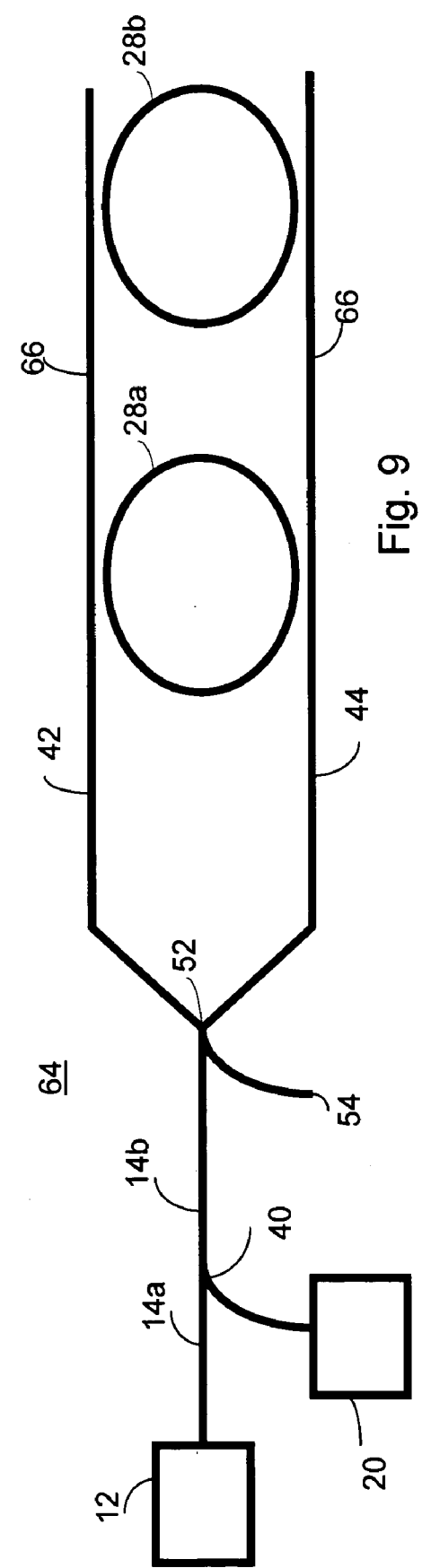

MICRO-RESONATOR BASED OPTICAL SENSOR

CROSS-REFERENCE TO RELATED APPLICATIONS

This application claims priority from U.S. Provisional Patent Application Ser. No. 60/494,570 filed Aug. 13, 2003 entitled "Micro-Resonator Based Optical Sensor" whose entire contents are incorporated herein by reference.

BACKGROUND OF THE INVENTION

The invention relates generally to the field of electro-optical devices and in particular to an optical sensor which provides an output signal as a function of a change in a sensed physical parameter such as pressure, temperature, absorption or motion.

Electro-optical devices have shown great promise in sensor applications. Passive optical sensors offer safe, accurate operation in hostile environments of heat and temperature, and are immune to electromagnetic interference. These advantages combine to make optically based sensors attractive for a number of applications.

A wide variety of optical sensing techniques have been suggested for measuring physical parameters. These devices however suffer from a lack of sensitivity, which is often required in modern sensors.

U.S. Pat. No. 4,475,812 issued to Buczek et al discloses an optical sensor with a gain medium situated at a first location, defining one end of a resonating optical cavity. An optical fiber couples electromagnetic radiation to a predetermined point at a second location, where it is directed toward a reflective surface, the reflective surface defining a second end of the resonating optical cavity. The physical condition to be sensed causes the reflective surface to move with respect to the end of the optical fiber. This movement essentially changes the length of the cavity in which the electromagnetic energy is resonating causing a corresponding change in the axial mode difference frequency within the cavity. Such a device requires a physical setup allowing for motion of the reflective surface with respect to the optical fiber, which may be difficult to accomplish. Furthermore, the sensitivity of such a sensor is limited by the ratio of the reflective surface travel to the total cavity length.

U.S. Pat. No. 4,775,214 issued to Johnson describes an optical sensor utilizing a single optical ring resonator having two independent resonant modes. The resonant frequencies of each of the resonant modes vary in different manners as the parameter to be measured changes. Such a device may be difficult to manufacture, in that it typically requires two independent resonant polarization modes whose resonant frequencies must vary in different manners in response to parameter changes. Furthermore, extraction of the parameter change requires complex characterization of the underlying sensor structure that is typically sensitive to process variations. The further requirement for a narrow bandwidth, variable frequency light beam source, adds additional cost and complexity, as such a source is sensitive to environmental changes and thus requires stabilization or control.

U.S. Pat. No. 6,278,811 issued to Hay et al. describes a fiber optic Bragg grating pressure sensor particularly suited for measuring ambient pressure of a fluid. Many sensor applications however are not centered on measuring the ambient pressure of a fluid, and a more flexible sensor is desirable.

U.S. Pat. No. 6,515,749 issued to Pipino discloses a chemical sensor, which includes an optical resonator including a nanostructured surface comprising a plurality of nanoparticles bound to one or more surfaces of the resonator. The nanoparticles provide optical absorption and the sensor further comprises a detector for detecting the optical absorption. The technique is somewhat limited to selective chemical interactions identifying the presence of target chemicals.

Thus there is a need for a method and apparatus combining high sensitivity with the ability to be adapted to a large variety of sensing applications.

SUMMARY OF THE INVENTION

Accordingly, it is a principal object of the present invention to overcome the disadvantages of prior art methods of optical sensors. This is provided in the present invention by the use of multiple resonator cavity loops exhibiting a sharp roll-off when the resonance condition is not met. At least one of the resonator cavity loops is reactive to an external parameter.

The invention provides for an optical sensor system for providing an output signal in response to a sensed parameter comprising: an optical signal source for generating an input optical signal; a sensing element in optical communication with the optical signal source, the sensing element comprising at least two resonant cavity loops exhibiting a common resonant frequency near at least one frequency of the input optical signal, at least one of the resonant cavity loops being exposed to an external parameter, the external parameter modifying the resonant frequency of the at least one exposed resonant cavity loop thereby modifying an optical output signal; and a detector in optical communication with the sensing element, the detector detecting any modification in the output optical signal in response to the sensed parameter.

In one preferred embodiment, the optical signal source generates an optical signal at a pre-determined frequency, the predetermined frequency being chosen so as to maximize the sensitivity of the sensing element. In a further preferred embodiment, the predetermined frequency is chosen so as to removed from the common resonant frequency of the at least two resonant cavity loops.

In one embodiment the optical signal source generates a swept optical signal over multiple optical frequencies, and in another embodiment the at least two resonant cavity loops are exposed to the external parameter, the external parameter modifying the resonant frequency of the exposed resonant cavity loops. In yet another embodiment the at least two resonant cavity loops are exposed to the external parameter, the external parameter further modifying the free spectral range of the exposed resonant cavity loops.

In an exemplary embodiment, the optical sensor system further comprises a reference resonant cavity loop, the reference resonant cavity loop filtering the optical input signal source prior to being input to the sensing element, whereby the sensing element receives a narrow bandwidth signal. In one further embodiment the optical signal source is a broadband light source. In another further embodiment the optical sensor system further comprises a tuning element operable to set the common resonant frequency of the reference resonant cavity loop. In a yet further embodiment the tuning element is operable to generate a swept optical signal over multiple optical frequencies.

In one embodiment the optical sensor system further comprises a reference arm; one of the resonator cavity loops being an interferometer reference resonator cavity loop disposed on the reference arm, and the at least one resonant cavity loop exposed to an external parameter defining the measurement arm of the interferometer. In one further embodiment the optical sensor system further comprises drop waveguides for each of the reference resonator cavity loop and the exposed resonator cavity loop. In another further embodiment, the optical sensor system further comprises a reference resonant cavity loop, the reference resonant cavity loop filtering the optical signal source prior to being input to the interferometer reference resonator cavity loop and the exposed resonator cavity loop. In a yet further embodiment the optical sensor system further comprises a tuning element operable to set the resonant frequency of the reference resonant cavity loop.

In one further embodiment, the measurement arm of the interferometer comprises at least two resonant cavity loops exposed to the external parameter, the external parameter modifying the resonant frequency of the exposed at least two resonant cavity loops. In a yet further embodiment, the optical sensor system further comprises at least two interferometer reference resonator cavity loops. In a yet further, further embodiment the number of the exposed resonator cavity loops is equal to the number of interferometer reference resonator cavity loops.

In one embodiment, the external parameter is at least one of pressure and temperature. In another embodiment the external parameter is the existence of a chemical substance, and preferably the sensing element further comprises a reacting chemically active substance, the reacting chemically active substance being chosen so as to modify the optical behavior of the exposed at least one resonant cavity loop in the presence of the chemical substance.

In yet another embodiment, the external parameter is motion within the plane of the exposed at least one resonant cavity loop. Preferably, the at least two resonant cavity loops are separated by a spacer, whereby no area of direct interaction is formed between the at least two resonant cavity loops. Preferably, at least one area of interaction is formed between the at least two resonant cavity loops, and wherein the same direction of propagation is maintained in the at least two resonant cavity loops. Further preferably, the direction of propagation is clockwise or counter-clockwise. In a preferred embodiment, the optical sensor system further comprises a transfer resonant cavity loop forming an area of interaction with each of the at least two resonant cavity loops.

The invention also provides for an optical sensor system for providing an output signal in response to a sensed parameter comprising: an optical signal source for generating an input optical signal; a reference resonator cavity loop in optical communication with the optical signal source; a tuning element operable in response to a tuning input to modify the resonant frequency of the reference resonator cavity loop; at least one resonant cavity loop exposed to an external parameter, the external parameter modifying the free spectral range of the exposed resonant cavity loop thereby modifying an optical output signal; and a detector in optical communication with the at least one resonant cavity loop, the detector detecting any modification in the free spectral range as a function of the tuning input in response to the sensed parameter. Preferably, the sensed parameter is at least one of temperature, pressure and the existence of a chemical substance.

The invention also provides for a method for providing an output signal in response to a sensed parameter comprising: receiving an input optical signal at a sensing element; modifying the resonant frequency of at least one resonant cavity loop of a plurality of resonant cavity loops of the sensing element in response to an external parameter, the plurality of resonant cavity loops having a common resonant frequency near at least one frequency of the input optical signal; modifying the input optical signal in response to the resonant frequency change thereby generating an output optical signal; detecting the output optical signal; and analyzing the output optical signal to determine a change in a sensed parameter.

In one embodiment, the input optical signal comprises a narrow frequency band, the narrow frequency band being selected so as to maximize the sensitivity of the sensing element. In a further embodiment, the narrow frequency band is selected to be removed from a common resonant frequency of the at least two resonant cavity loops.

In another embodiment the optical signal comprises an optical signal swept over multiple optical frequencies. In yet another embodiment the stage of modifying the resonant frequency is accomplished on at least two resonant cavity loops being exposed to the parameter, the parameter modifying the resonant frequency of the at least two exposed resonant cavity loops.

In another embodiment, the method further comprises filtering the input optical signal prior to the receiving an input signal, whereby, the sensing element receives a narrow bandwidth signal. In a further embodiment, the method comprises tuning of the filtering, the tuning of the filtering being operable to sweep the filtered optical input signal over multiple optical frequencies. In a yet further embodiment, the stage of analyzing further comprises analyzing the output signal as a function of the tuning.

In one embodiment, the method further comprises tuning of the plurality of resonant cavity loops to a common resonant frequency. In another embodiment the sensed parameter is at least one of pressure and temperature. In yet another embodiment the sensed parameter is the existence of a chemical substance. In a further embodiment, the stage of modifying the resonant frequency comprises reacting a chemically active substance chosen so as to modify the optical behavior of the at least one resonant cavity loop in the presence of the chemical substance.

In another embodiment the sensed parameter is motion within the plane of the plurality of resonant cavity loops. In a further embodiment, the method further comprises forming an area of interaction between at least two resonant cavity loops, and wherein the same direction of propagation is maintained in the at least two resonant cavity loops. In a yet further embodiment the direction of propagation is clockwise or counter-clockwise.

The invention also provides for an optical sensor for providing an output signal in response to a sensed parameter comprising: a reference resonator cavity loop; a resonant cavity loop exposed to an external parameter, the external parameter modifying the free spectral range or the resonant frequency of the exposed resonant cavity loop. In a preferred embodiment, the optical sensor further comprises a tuning element operable to modify the resonant frequency of the reference resonator cavity loop.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 1 illustrates a high level block diagram of a sensing system in accordance with the teaching of the invention;

FIG. 2 illustrates a high level block diagram of a sensing element in accordance with the teaching of the invention;

FIG. 3a illustrates a high level block diagram of a first embodiment of an improved sensing element in accordance with the teaching of the invention;

FIG. 4b illustrates a high level block diagram of a second embodiment of an interferometer based sensing element comprising a reference arm in accordance with the teaching of the invention;

FIG. 4c illustrates a high level block diagram of a third embodiment of an interferometer based sensing element comprising a reference arm in accordance with the teaching of the invention;

FIG. 5b illustrates a high level block diagram of a fifth embodiment of an interferometer based sensing element comprising a reference arm in accordance with the teaching of the invention;

FIG. 6 illustrates a high level block diagram of a first embodiment of an optical gyroscope in accordance with the teaching of the invention;

FIG. 7 illustrates a high level block diagram of a second embodiment of an optical gyroscope in accordance with the teaching of the invention;

FIG. 8 illustrates a high level block diagram of a third embodiment of an optical gyroscope in accordance with the teaching of the invention; and FIG. 9 illustrates a high level block diagram of a fourth embodiment of an optical gyroscope in accordance with the teaching of the invention.

DETAILED DESCRIPTION OF THE PREFERRED EMBODIMENTS

Figure 3B:
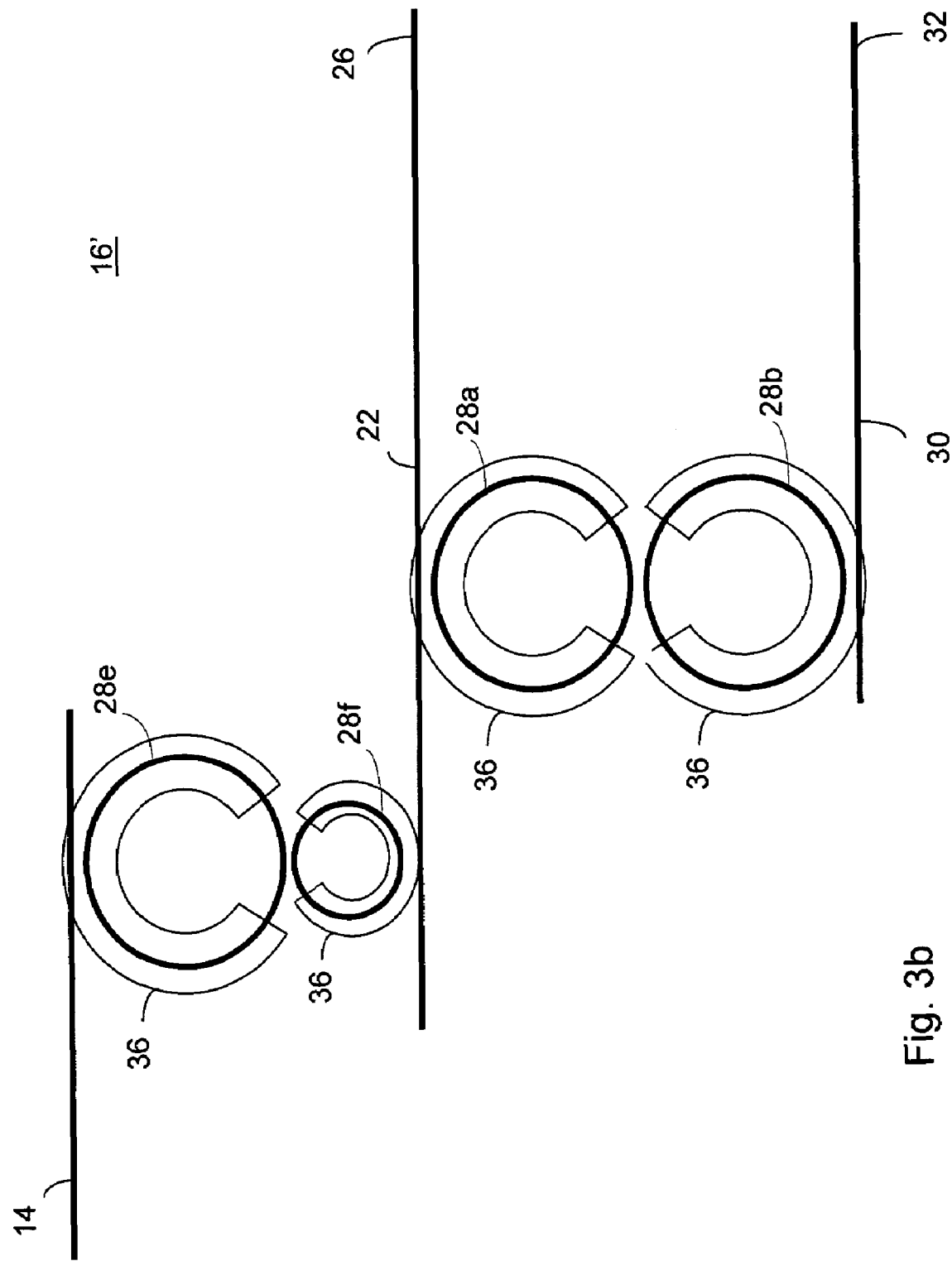
FIG. 3b illustrates a high level block diagram of a second embodiment of an improved sensing element in accordance with the teaching of the invention.

The present embodiments enable a method and apparatus for optical sensing which provides a highly sensitive output signal representative of a sensed parameter that is adaptable to a large variety of sensing applications. The present invention utilizes multiple resonator cavity loops, which in combination exhibit sharp roll off when the resonance condition is not met. In another embodiment at least one resonator cavity loop is utilized as a sensor, and at least a second resonator cavity loop is used as an interferometer reference resonator.

In yet another embodiment at least one resonator cavity loop is utilized as sensor, and at least a second resonator cavity loop in combination with a tuning element is used as a reference. A broadband fixed optical source is used in combination with a tuning element, the tuning element being operable to set the resonant frequency of the reference resonator cavity loop over a range of frequencies, with the output of the reference resonator cavity loop being input to the sensor resonator cavity loop. In one further embodiment, the optical source bandwidth is greater than twice the free spectral range of the sensor resonator cavity loop, and the detector is operable to detect the differences in resonance frequencies as a function of the input to the tuning element.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates a high level block diagram of a sensing system 10 in accordance with the teaching of the invention. Sensing system 10 comprises transmitter 12, first optical waveguide 14, sensing element 16, second optical waveguide 18 and detector 20. The output of transmitter 12 is connected to one end of first optical waveguide 14 and the second end of first optical waveguide 14 is connected to the input of sensing element 16. The output of sensing element 16 is connected to one end of second optical waveguide 18, and the second end of second optical waveguide 18 is connected to the input of detector 20. In one embodiment both first optical waveguide 14 and second optical waveguide 18 comprise a single optical waveguide. In a preferred embodiment sensing element 16 further comprises tuning means (not shown) such as a heating element, piezo, voltage source or other stress source.

In a first preferred operation, transmitter 12 outputs an optical signal that propagates through first optical waveguide 14 to sensing element 16. In one further preferred embodiment, transmitter 12 comprises a narrow band source. In another further preferred, which will be described further herein to below, embodiment transmitter 12 comprises a broad band source, the broad band being narrower than the free spectral range (FSR) of sensing element 16. Sensing element 16 may be connected in a one of a number of configurations as will be described further below. The output of sensing element 16 propagates through second optical waveguide 18 and is received at detector 20, which operates to detect a minimum, a maximum or a changed reading in accordance with the predetermined connection pattern of sensing element 16. In one embodiment, tuning means (not shown), is operable to tune the resonant frequency of the sensing element 16 to be at, or near, the frequency of the optical signal prior to measurement.

In a second preferred operation, transmitter 12 is swept over a range of wavelengths, and the optical swept wavelength signal propagates through optical waveguide 14 to sensing element 16. The output of sensing element 16 propagates through second optical waveguide 18 and is received at detector 20, which operates to detect the response pattern of sensing element 16 as a function of wavelength. Any change in the response pattern as a function of wavelength from an initial response in either amplitude or phase, or a combination thereto, is detected and translated to an electrical output in response to the change. The initial response may be a calibrated response, an initial steady state response, a reference response, or an arbitrary value or point in time chosen as a base.

FIG. 2 illustrates a high level block diagram of sensing element 16 in accordance with the teaching of the invention. Sensing element 16 comprises first optical waveguide 22 having input 24 and output 26, sensing resonator cavity loop 28 and second optical waveguide 30 having input 34 and output 32, and optional tuning element 36. First optical waveguide 22 is placed in close proximity to at least a portion of sensing resonator cavity loop 28 thus creating a first interaction area of evanescent coupling. Optional tuning element 36 is placed in proximity of sensing resonator cavity loop 28 so as to tune the resonant frequency thereof. Second optical waveguide 30 is placed in close proximity to at least a portion of sensing resonator cavity loop 28 thus creating a second interaction area of evanescent coupling.

Details of the evanescent coupling between an optical signal traversing optical waveguide 22, 30 and sensing resonator cavity loop 28 are described in detail in U.S. Pat. No. 6,052,495 issued to Little et al, in "MicroRing Resonator Channel Dropping Filters", B. E. Little, S. T. Chu, H. A. Haus, J. Forsei and J. P. Laine—Journal of Lightwave Technology, 1997, Vol. 15, No. 6, pp. 998–1005; and in "A Wide FSR Waveguide Double-ring Resonator for Optical FDM Transmission Systems", K. Oda, N. Takato and H. Toba—Journal of Lightwave Technology, 1991, Vol. 9, No. 6, pp 728–736, whose contents are incorporated herein by reference.

In order for sensing resonator cavity loop 28 to measure temperature or pressure, sensing resonator cavity loop 28 is exposed to the environment or pressure source. In an exemplary embodiment this is accomplished by opening a window to allow sensing resonator cavity loop 28 to be in contact with the environment or pressure source. In another exemplary embodiment sensing resonator cavity loop 28 is utilized to detect the presence or absence of a specific chemical by the deposition of a pre-determined chemically active substance directly on sensing resonator cavity loop 28. The pre-determined chemically active substance is then made to be in contact with, or accessible to, the material or gas under test, preferably through an open window. The pre-determined chemically active substance is selected to react in response to the presence or absence of the specific chemical to be detected and exhibit a modified optical behavior, and as a result modify the optical behavior of sensing resonator cavity loop 28.

In operation, an optical signal propagating in first optical waveguide 22 is coupled to sensing resonator cavity loop 28, and optical energy coupled to sensing resonator cavity loop 28 is further coupled to second optical waveguide 30. At the resonant condition, in which the frequency of the optical signal matches a resonant frequency of sensing resonator cavity loop 28, a maximum amount of energy is coupled from first optical waveguide 22 to second optical waveguide 30 and appears at output 32, while a minimal amount of energy appears at output 26. Input 34 is shown for completeness, since sensing resonator cavity loop 28 operates bi-directionally. Thus, at the resonant condition, for input energy appearing at input 34 of second optical waveguide 30, a maximum amount of energy is coupled to first optical waveguide 22 and appears at output 26, while a minimal amount of energy appears at output 32.

As described above, at the resonant condition, the maximum amount of energy will appear at output 32, and consequently the minimum amount of energy will appear at output 26. Waveguide 30 is also known as the drop waveguide, in that some or all of the energy at the resonant frequency is dropped from waveguide 22 to waveguide 30. The precise amount of energy is a function of the interaction between first optical waveguide 22 and sensing resonator cavity loop 28, the interaction between second optical waveguide 30 and sensing resonator cavity loop 28, and the structure of sensing resonator cavity loop 28. In a preferred embodiment, sensing element 16 further comprises optional tuning means 36, comprising a heating element, piezo, voltage source or other stress source, operable to set one of the resonant frequencies of sensing resonator cavity loop 28 near or at the frequency of the optical signal output by transmitter 12 of FIG. 1, prior to operation of sensing element 16. In an alternative preferred embodiment the wavelength of transmitter 12 is controlled by feedback from detector 20 to transmit at the initial resonant frequency of resonator cavity loop 28, thus ensuring operation of sensing element 16 at or near the initial resonant frequency without the requirement for optional tuning element 36. Changes in the resonant condition due to external parameters such as temperature or pressure will affect the resonant condition and thus the amount of energy appearing at outputs 26 and 32. The existence of certain chemicals will act to change the optical behavior of sensing resonator cavity loop 28, by a reaction of a chemically active substance as described above, thereby also affecting the resonance condition. For such chemicals, sensing element 16 will act as a sensor indicating the existence or absence of such chemical by any changes in the resonant condition of sensing resonator cavity loop 28.

Input 24 of first optical waveguide 22 is coupled to the second end of first optical waveguide 14 of FIG. 1 at the input to sensing element 16, thus operatively connecting sensing element 16 to transmitter 12. In a first preferred configuration, output 26 of first optical waveguide 22 is coupled at the output of sensing element 16 to one end of second optical waveguide 18 of FIG. 1, thus operatively connecting an output of sensing element 16 to detector 20. A minimum amount of energy is thus detected at the resonant condition by detector 20. In a second preferred configuration, output 32 of second optical waveguide 30 is coupled at the output of sensing element 16 to one end of second optical waveguide 18 of FIG. 1, thus operatively connecting an output of sensing element 16 to detector 20. A maximum amount of energy at the resonant condition is detected by detector 20.

In an exemplary embodiment, of both the first and second preferred configuration, transmitter 12 is operated at a frequency that is offset by a pre-determined amount from the initial resonance frequency of sensing resonator cavity loop 28, thus increasing the sensitivity of sensing element 16. The pre-determined offset from the initial resonance frequency is selected so as to ensure operation within the steep slope response range of sensing element 16. Such an offset is preferred, since for a sensing resonator cavity loop operating at resonance, a small perturbation will not be as easily detected as a small perturbation in the steep roll-off area of a sensing resonator cavity loop. It is to be understood by those skilled in the art that the condition of being off resonance can be accomplished by adjusting the frequency of transmitter 12, or by adjusting the resonant frequency of sensing resonator cavity loop 28 by the operation of optional tuning element 36, without exceeding the scope of the invention.

In a first preferred operation of sensing system 10 of FIG. 1, detector 20 detects a change in amplitude in response to an external parameter. In a second preferred operation, detector 20 detects a change in phase in response to an external parameter. In a third preferred operation, a change in both amplitude and phase in response to an external parameter are detected by detector 20.

The above has been explained in an embodiment in which transmitter 12 is operated at a specific fixed wavelength, however this is not meant to be limiting in any way. In an alternative embodiment, transmitter 12 is swept over a range of wavelengths and detector 20 is operated to detect a change in the response curve of sensing element 16. A change in the response pattern as a function of wavelength, as compared to an initial response, or in respect to an identical resonator used as a reference, in either amplitude or phase, or a combination thereto, is detected and translated to an electrical output by detector 20, in response to the change. The initial response may be a calibrated response, an initial steady state response, the response of the reference, or an arbitrary value or point in time chosen as a base.

FIG. 3a illustrates a high level block diagram of a first embodiment of an improved sensing element 16' exhibiting enhanced sensitivity as compared with sensing element 16 of FIG. 2. Improved sensing element 16' is operable to replace sensing element 16 of FIG. 1 and to be operable as part of sensing system 10. Sensing element 16' comprises first optical waveguide 22 having input 24 and output 26, first sensing resonator cavity loop 28a, second sensing resonator cavity loop 28b, optional first and second tuning elements 36, and second optical waveguide 30 having input 34 and output 32. First optical waveguide 22 is placed in close proximity to at least a portion of first sensing resonator cavity loop 28a thus creating a first interaction area of evanescent coupling. At least a portion of second sensing resonator cavity loop 28b is placed in close proximity to at least a portion of first sensing resonator cavity loop 28a thus creating a second interaction area of evanescent coupling. Second waveguide 30 is placed in close proximity to at least a portion of second sensing resonator cavity loop 28b thus creating a third interaction area of evanescent coupling. Optional first tuning element 36 is placed in proximity to first sensing resonator cavity loop 28a so as to tune the resonant frequency thereof, and optional second tuning element 36 is placed in proximity of second sensing resonator cavity loop 28b so as to tune the resonant frequency thereof.

In operation, an optical signal propagating in first optical waveguide 22 is coupled to first sensing resonator cavity loop 28a, and optical energy coupled to first sensing resonator cavity loop 28a is coupled to second sensing resonator cavity loop 28b. Optical energy in second sensing resonator cavity loop 28b is further coupled to second optical waveguide 30. At the common resonant frequency of first sensing resonator cavity loop 28a and second sensing resonator cavity loop 28b, a maximum amount of energy appearing at input 24 of first optical waveguide 22 at the common resonant frequency is coupled from first optical waveguide 22 to second optical waveguide 30 and appears finally at output 32. As described above, waveguide 30 is thus known as the drop waveguide. Similarly, at a common resonant frequency of first sensing resonator cavity loop 28a and second sensing resonator cavity loop 28b, a minimum amount of energy at the common resonant frequency appearing at input 24 appears at output 26. Input 34 is shown for completeness; since sensing resonator cavity loops 28a and 28b operate bi-directionally. Thus input energy appearing at input 34 of second optical waveguide 34 will be coupled to first optical waveguide 22 and appear at output 26. It is to be understood that in practice the resonant frequencies of first sensing resonator cavity loop 28a and second sensing resonator cavity loop 28b are typically not identical, and need to be set to a common resonant frequency by operation of optional first and second tuning elements 36, or otherwise must be manufactured under strict conditions.

Sensing element 16' operates in a manner similar to that of sensing element 16 of FIG. 2 with the added benefit of having a sharper Q, or roll-off. Thus sensing element 16' is significantly more sensitive to changes in external parameters than sensing element 16. Preferably, transmitter 12 is operated at a pre-determined offset from the common resonance condition of sensing resonator cavity loops 28a and 28b. Sensing element 16' is shown having two sensing resonator cavity loops 28a and 28b, however this is not meant to be limiting in any way. Additional cascaded sensing resonator cavity loops may be utilized to further increase the sensitivity of sensing element 16' without exceeding the scope of the invention. The addition of further cascaded sensing resonator cavity loops increases the sensitivity following a power law function.

In order for sensing resonator cavity loops 28a and 28b to measure temperature or pressure, sensing resonator cavity loops 28a and 28b are exposed to the environment or pressure source. In an exemplary embodiment this is accomplished by opening a window to allow sensing resonator cavity loops 28a and 28b to be in contact with the environment or pressure source. In another exemplary embodiment sensing resonator cavity loops 28a and 28b are utilized to detect the presence or absence of a specific chemical by the deposition of a pre-determined reacting chemically active substance directly on sensing resonator cavity loops 28a and 28b. The pre-determined reacting chemically active substance is then made to be in contact with, or accessible to, the material or gas under test, preferably through an open window. The pre-determined reacting chemically active substance is selected to exhibit a modified optical behavior, and as a result modify the optical behavior of sensing resonator cavity loops 28a and 28b in response to the presence or absence of the specific chemical to be detected.

In one exemplary embodiment, transmitter 12 of FIG. 1 is operated at a wavelength chosen to maximize the sensitivity of sensing element 16' to changes in the external parameter. Preferably, such a wavelength is close to, but removed from, the common resonant frequency of sensing resonator cavity loops 28a and 28b. The condition of being off resonance can be accomplished by adjusting the frequency of transmitter 12, or by adjusting the common resonant frequency of sensing resonator cavity loop 28a and 28b by the operation of optional first and second tuning elements 36, without exceeding the scope of the invention. In another exemplary embodiment, transmitter 12 is swept over a range of wavelengths chosen to include wavelengths around the resonant condition area. Changes in the response curve of sensing element 16' are detected by detector 20 and converted to an electrical response. Any change in the response pattern as a function of wavelength from an initial response in either amplitude or phase, or a combination thereto, is detected and translated to an electrical output in response to the change. The initial response may be a calibrated response, an initial steady state response, a reference response, or an arbitrary value or point in time chosen as a base.

In a first preferred configuration of sensing system 10 of FIG. 1 utilizing sensing element 16', output 26 of first optical waveguide 22 is coupled at the output of sensing element 16' to one end of second optical waveguide 18, thus operatively connecting an output of sensing element 16' to detector 20. A minimum amount of energy is thus detected at the resonant condition by detector 20. In a second preferred configuration of sensing system 10 of FIG. 1 utilizing sensing element 16', output 32 of second optical waveguide 30 is coupled at the output of sensing element 16' to one end of second optical waveguide 18, thus operatively connecting an output of sensing element 16 to detector 20. A maximum amount of energy is thus detected at the resonant condition by detector 20.

FIG. 3b illustrates a high level block diagram of a second embodiment of an improved sensing element 16' exhibiting enhanced sensitivity. Improved sensing element 16' is operable to replace sensing element 16 of FIG. 1 and to be operable as part of sensing system 10. Sensing element 16' comprises input optical waveguide 14, reference resonator cavity loops 28e, 28f, optional first and second tuning elements 36, first optical waveguide 22 having output 26, first sensing resonator cavity loop 28a, second sensing resonator cavity loop 28b, optional third and fourth tuning elements 36, and second optical waveguide 30 having output 32. Input optical waveguide 14 is placed in close proximity to at least a portion of first reference resonator cavity loop 28e thus creating a first interaction area of evanescent coupling. First reference resonator cavity loop 28e is placed in close proximity to at least a portion of second reference resonator cavity loop 28f, thus creating a second interaction area of evanescent coupling. Second reference resonator cavity loop 28f is placed in close proximity to at least a portion of first optical waveguide 22 thus creating a third interaction area of evanescent coupling. Optional first tuning element 36 is placed in proximity to first reference resonator cavity loop 28e so as to tune the resonant frequency thereof, and optional second tuning element 36 is placed in proximity of second reference resonator cavity loop 28f so as to tune the resonant frequency thereof. First optical waveguide 22 is placed in close proximity to at least a portion of first sensing resonator cavity loop 28a thus creating a fourth interaction area of evanescent coupling. At least a portion of second sensing resonator cavity loop 28b is placed in close proximity to at least a portion of first sensing resonator cavity loop 28a thus creating a fifth interaction area of evanescent coupling. Optional third tuning element 36 is placed in proximity to first sensing resonator cavity loop 28a so as to tune the resonant frequency thereof, and optional fourth tuning element 36 is placed in proximity of second sensing resonator cavity loop 28b so as to tune the resonant frequency thereof. Second optical waveguide 30 is placed in close proximity to at least a portion of second sensing resonator cavity loop 28b thus creating a sixth interaction area of evanescent coupling.

In operation, sensing element 16' of FIG. 3b operates similarly to that of sensing element 16' of FIG. 3a with the notable exception of the use of reference resonators 28e and 28f to create a narrow frequency filter. An optical signal propagating in input optical waveguide 14 is coupled at the common resonant frequency of reference resonators 28e and 28f to first optical waveguide 22. Second reference resonator 28f is shown to be of a different size than first reference resonator 28e, thus with appropriate tuning utilizing optional first and second tuning elements 36, a mutual common resonance can be found. In an exemplary embodiment the combination of reference resonator 28e and 28f exhibit only a single narrow common resonance over the bandwidth of transmitter 12, and thus only a single narrow bandwidth is transferred to first optical waveguide 22. Transmitter 12 of FIG. 1 can therefore be a reduced cost broadband light source without impacting the sensitivity of sensing element 16'. In another embodiment, optional first and second tuning elements are operated to sweep the common resonance frequency of first and second reference resonators 28e and 28f over a range of frequencies, thus allowing transmitter 12 to comprise a single low cost broadband source.

In a first preferred configuration of sensing system 10 of FIG. 1 utilizing sensing element 16' of FIG. 3b, output 26 of first optical waveguide 22 is coupled at the output of sensing element 16' to one end of second optical waveguide 18, thus operatively connecting an output of sensing element 16' to detector 20. A minimum amount of energy is thus detected at the resonant condition by detector 20. In a second preferred configuration of sensing system 10 of FIG. 1 utilizing sensing element 16', output 32 of second optical waveguide 30 is coupled at the output of sensing element 16' to one end of second optical waveguide 18, thus operatively connecting an output of sensing element 16 to detector 20. A maximum amount of energy is thus detected at the resonant condition by detector 20.

In an exemplary embodiment of both the first and second configurations, the common resonant frequency of reference resonators 28e and 28f is chosen to be close to, but removed from, the common resonant frequency of sensing resonator cavity loops 28a and 28b. Reference resonators 28e and 28f thus serve as a reference to the absolute frequency shift caused by the external parameter being detected by detector 20. As described above the resonant frequency of first reference resonator 28e is modified by the operation of optional first tuning element 36, and the resonant frequency of second reference resonator 28f is modified by the operation of optional second tuning element 36.

Figure 3C:
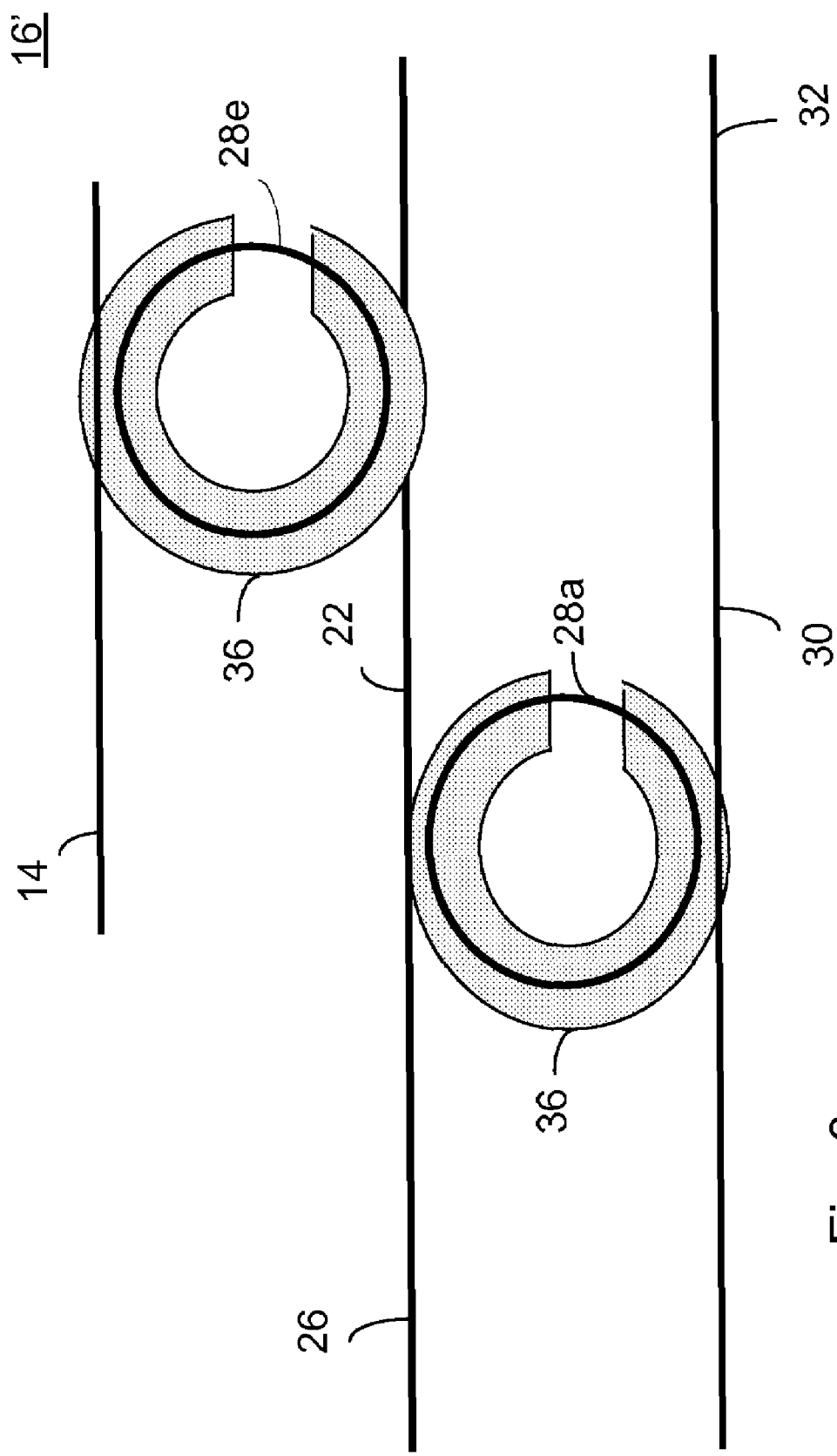
FIG. 3c illustrates a high level block diagram of a third embodiment of an improved sensing element in accordance with the teaching of the invention.

FIG. 3c illustrates a high level block diagram of a third embodiment of an improved sensing element 16' exhibiting enhanced sensitivity. Improved sensing element 16' is operable to replace sensing element 16 of FIG. 1 and to be operable as part of sensing system 10. Sensing element 16' comprises input optical waveguide 14, reference resonator cavity loop 28e, first tuning element 36, first optical waveguide 22 having output 26, sensing resonator cavity loop 28a, optional second tuning element 36, and second optical waveguide 30 having output 32. Input optical waveguide 14 is placed in close proximity to at least a portion of reference resonator cavity loop 28e thus creating a first interaction area of evanescent coupling. First reference resonator cavity loop 28e is placed in close proximity to at least a portion of first optical waveguide 22 thus creating a second interaction area of evanescent coupling. First tuning element 36 is placed in proximity to reference resonator cavity loop 28e so as to tune the resonant frequency thereof. First optical waveguide 22 is placed in close proximity to at least a portion of sensing resonator cavity loop 28a thus creating a third interaction area of evanescent coupling. Optional second tuning element 36 is placed in proximity to sensing resonator cavity loop 28a so as to tune the resonant frequency thereof. Second optical waveguide 30 is placed in close proximity to at least a portion of sensing resonator cavity loop 28a thus creating a fourth interaction area of evanescent coupling.

In operation, sensing element 16' of FIG. 3c operates similarly to that of sensing element 16' of FIG. 3b with the notable exception that first tuning element 36 is not optional. Only a single reference resonator cavity loop 28e and a single sensing resonator cavity loop 28a is show, however this is not meant to be limiting in any way. Multiple reference resonators may be used without exceeding the scope of the invention. Similarly, multiple sensing resonator cavity loops may be used without exceeding the scope of the invention. Transmitter 12 of FIG. 1 is a reduced cost broadband light source, and reference resonator 28e operates as a frequency filter, which is tuned by operation of first tuning element 36, with the input to first tuning element 36 being monitored as an input to detector 20. An optical signal propagating in input optical waveguide 14 is coupled at the resonant frequency of reference resonator 28e to first optical waveguide 22.

In a first preferred configuration of sensing system 10 of FIG. 1 utilizing sensing element 16' of FIG. 3c, output 26 of first optical waveguide 22 is coupled at the output of sensing element 16' to one end of second optical waveguide 18, thus operatively connecting an output of sensing element 16' to detector 20. A minimum amount of energy is thus detected at the resonant condition by detector 20. In this first preferred configuration, second optical waveguide 30 is not required. In a second preferred configuration of sensing system 10 of FIG. 1 utilizing sensing element 16', output 32 of second optical waveguide 30 is coupled at the output of sensing element 16' to one end of second optical waveguide 18, thus operatively connecting an output of sensing element 16 to detector 20. A maximum amount of energy is thus detected at the resonant condition by detector 20.

In a first exemplary embodiment of both the first and second configurations, the resonant frequency of reference resonators 28e is swept across a range of frequencies, and detector 20 thus detects the response curve as a function of the input to first tuning element 36. Initial calibration of detector 20 includes a conversion of first tuning element 36 input to output frequency, thus calculating the response curve of sensing element 16' as a function of frequency.

The free spectral range (FSR) of resonator cavity loop is defined as the frequency separation of adjacent resonances. In a second exemplary embodiment of both the first and second configurations, the resonant frequency of reference resonator 28e is swept across a range of frequencies, the range of frequencies including multiple FSR's of the sensing resonator. Initial calibration of detector 20 includes a conversion of first tuning element 36 input to output frequency, thus calculating the response curve of sensing element 16' as a function of frequency. The FSR of sensing resonator cavity loop 28a varies in response to the external parameter being detected, and detector 20 thus detects the response curve as a function of input to first tuning element 36, and outputs any change in the FSR of sensing resonator cavity loops 28a.

Figure 4A:
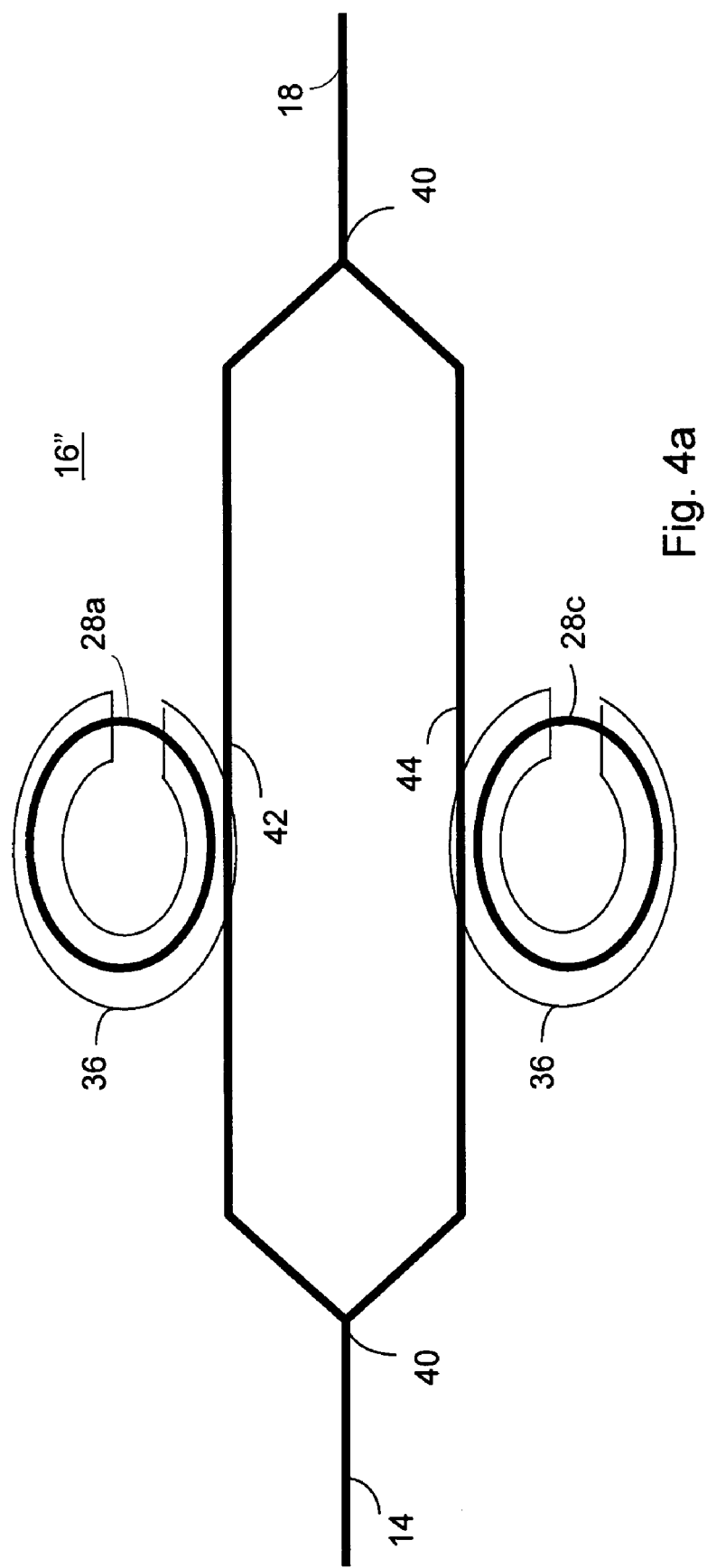
FIG. 4a illustrates a high level block diagram of a first embodiment of an interferometer based sensing element comprising a reference arm in accordance with the teaching of the invention.

FIG. 4a illustrates a high level block diagram of a first embodiment of an interferometer based sensing element 16" comprising sensing resonator cavity loop 28a and interferometer reference resonator cavity loop 28c. Improved sensing element 16" is operable to replace sensing element 16 of FIG. 1 and to be operable as part of sensing system 10. Sensing element 16" comprises input optical waveguide 14, splitters 40, first optical waveguide 42, second optical waveguide 44, sensing resonator cavity loop 28a, interferometer reference resonator cavity loop 28c, optional first and second tuning elements 36, and output optical waveguide 18. Input optical waveguide 14 is connected to the input of first splitter 40, and a first split output of first splitter 40 is connected to one end of first optical waveguide 42. The second split output of first splitter 40 is connected to one end of second optical waveguide 44. First optical waveguide 42 is placed in close proximity to at least a portion of sensing resonator cavity loop 28a, thus creating a first interaction area of evanescent coupling. Optional first tuning element 36 is placed in proximity to sensing resonator cavity loop 28a so as to tune the resonant frequency thereof. Second optical waveguide 44 is placed in close proximity to at least a portion of interferometer reference resonator cavity loop 28c, thus creating a second interaction area of evanescent coupling. Optional second tuning element 36 is placed in proximity to interferometer reference resonator cavity loop 28c so as to tune the resonant frequency thereof. The second end of first optical waveguide 42 is connected to a first split input of second splitter 40, and the second end of second optical waveguide 44 is connected to a second split input of second splitter 40. The output of second splitter 40 is connected to one end of output optical waveguide 18.

In operation, sensing element 16" operates as an interferometer, with interferometer reference resonator cavity loop 28c acting as the reference arm. Sensing resonator cavity loop 28a operatively reacts to changes in external parameters such as temperature, pressure or the presence or absence of a specific chemical. Any change in the resonance condition of sensing resonator cavity loop 28a will result in a changed interference pattern in output optical waveguide 18 caused by the difference between the resonant frequency of sensing resonator cavity loop 28a and interferometer reference resonator cavity loop 28c. The interference is based on the difference in phase between the portions of the optical signal traveling in optical waveguides 42 and 44, and is significantly more sensitive to parameter changes than the amplitude variations discussed in relation to sensor 16 and 16' of FIGS. 2, 3a, 3b and 3c respectively. The interference pattern in optical waveguide 18 is detected by detector 20 of FIG. 1 that is connected to a second end of optical waveguide 18.

In the embodiment of sensing element 16" shown in FIG. 4a, transmitter 12 of FIG. 1 comprises a narrow band optical source, thus improving the sensitivity of detector 20 which will thus only receive interference patterns over a narrow bandwidth. Further preferably, transmitter 12 operates at the resonant frequency of reference resonator cavity loop 28c. Optional first and second tuning elements 36 are operable to ensure a common resonance frequency of sensing resonator cavity loop 28a and interferometer reference resonator cavity loop 28c. Sensing element 16" is only operable over a narrow bandwidth, and thus in an exemplary embodiment operation of sensing element 16" is improved by the use of optional second tuning element 36, which functions to maintain a fixed interference pattern in output optical waveguide 18. The fixed interference pattern may be a calibrated response, an initial steady state response, a reference response, or an arbitrary value or point in time chosen as a base. Changes to the input of optional second tuning element 36 are tracked by detector 20, and the change in input to optional second tuning element 36 required to maintain the fixed interference pattern, thus tracking the change in the phase of sensing resonator cavity loop 28a, is converted to an output representing the sensed parameter.

In order for sensing resonator cavity loop 28a to measure temperature or pressure, sensing resonator cavity loop 28a is exposed to the environment or pressure source. In an exemplary embodiment this is accomplished by opening a window to allow sensing resonator cavity loop 28a to be in contact with the environment or pressure source. In another exemplary embodiment sensing resonator cavity loop 28a is utilized to detect the presence or absence of a specific chemical by the deposition of a pre-determined reacting chemically active substance directly on sensing resonator cavity loop 28a. The pre-determined reacting chemically active substance is then made to be in contact with, or accessible to, the material or gas under test, preferably through an open window. The pre-determined reacting chemically active substance is chosen to change its optical behavior, and as a result the optical behavior of sensing resonator cavity loop 28a in response to the presence or absence of the specific chemical.

In a preferred embodiment, sensing element 16" self compensates for changes in temperature and other environmental effects which are not being sensed. Sensing resonator cavity loop 28a and interferometer reference resonator cavity loop 28c are placed on a single block of silicon, and thus are equally affected by global environmental effects. This is particularly relevant for applications in which sensing element 16" is utilized to detect for presence or absence of a specific chemical, or where pressure changes are to be sensed.

FIG. 4b illustrates a high level block diagram of a second embodiment of an interferometer based sensing element 16" comprising sensing resonator cavity loop 28a and interferometer reference resonator cavity loop 28c, in which a drop waveguide is utilized. Improved sensing element 16" is operable to replace sensing element 16 of FIG. 1 and to be operable as part of sensing system 10. Sensing element 16" comprises input optical waveguide 14, splitters 40, first optical waveguide 42, second optical waveguide 44, third optical waveguide 46, fourth optical waveguide 48, sensing resonator cavity loop 28a, interferometer reference resonator cavity loop 28c, optional first and second tuning elements 36, and output optical waveguide 18. Input optical waveguide 14 is connected to the input of first splitter 40, and a first split output of first splitter 40 is connected to one end of first optical waveguide 42. A second split output of first splitter 40 is connected to one end of second optical waveguide 44. First optical waveguide 42 is placed in close proximity to at least a portion of sensing resonator cavity loop 28a, thus creating a first interaction area of evanescent coupling. Optional first tuning element 36 is placed in proximity to sensing resonator cavity loop 28a so as to tune the resonant frequency thereof. Second optical waveguide 44 is placed in close proximity to at least a portion of interferometer reference resonator cavity loop 28c, thus creating a second interaction area of evanescent coupling. Optional second tuning element 36 is placed in proximity to interferometer reference resonator cavity loop 28c so as to tune the resonant frequency thereof. Third optical waveguide 46 is placed in close proximity to at least a portion of interferometer reference cavity loop 28c, thus creating a third interaction area of evanescent coupling. Fourth optical waveguide 48 is placed in close proximity to at least a portion of sensing resonator cavity loop 28a, thus creating a fourth interaction area of evanescent coupling. One end of third optical waveguide 46 is connected to a first split input of second splitter 40, and one end of fourth optical waveguide 48 is connected to a second split input of second splitter 40. The output of second splitter 40 is connected to one end of output optical waveguide 18.

In operation, sensing element 16" of FIG. 4b operates similarly to that of sensing element 16" of FIG. 4a with the notable exception that the drop waveguides 46 and 48 are utilized. Advantageously, only energy at the common resonant frequency of sensing resonator cavity loop 28a and interferometer reference cavity loop 28c appear at output waveguide 18 and are received by detector 20, thus transmitter 12 of FIG. 1 can be a reduced cost broadband light source without impacting the sensitivity of sensing element 16".

FIG. 4c illustrates a high level block diagram of a third embodiment of an interferometer based sensing element 16" comprising reference resonators 28e and 28f, sensing resonator cavity loop 28a and interferometer reference resonator cavity loop 28c. Improved sensing element 16" is operable to replace sensing element 16 of FIG. 1 and to be operable as part of sensing system 10. Sensing element 16" comprises input optical waveguide 14, reference resonators 28e and 28f, splitters 40, first optical waveguide 22, second optical waveguide 42, third optical waveguide 44, sensing resonator cavity loop 28a, interferometer reference resonator cavity loop 28c, optional tuning elements 36, and output optical waveguide 18. Input optical waveguide 14 is placed in close proximity to at least of portion of first reference resonator cavity loop 28e, thus creating a first area of evanescent coupling. Optional first tuning element 36 is placed in proximity to first reference resonator cavity loop 28e so as to tune the resonant frequency thereof. At least a portion of first reference resonator cavity loop 28e is placed in close proximity to at least a portion of second reference resonator cavity loop 28f, thus creating a second area of evanescent coupling. Optional second tuning element 36 is placed in proximity to second reference resonator cavity loop 28f so as to tune the resonant frequency thereof. A portion of first optical waveguide 22 is placed in close proximity to at least a portion of second reference resonator cavity loop 28f thus creating a third area of evanescent coupling. One end of first optical waveguide 22 is connected to the input of first splitter 40, and a first split output of first splitter 40 is connected to one end of second optical waveguide 42. Second split output of first splitter 40 is connected to one end of third optical waveguide 44. Second optical waveguide 42 is placed in close proximity to at least a portion of sensing resonator cavity loop 28a, thus creating a fourth interaction area of evanescent coupling. Optional third tuning element 36 is placed in proximity to sensing resonator cavity loop 28a so as to tune the resonant frequency thereof. Third optical waveguide 44 is placed in close proximity to at least a portion of interferometer reference resonator cavity loop 28c, thus creating a fifth interaction area of evanescent coupling. Optional fourth tuning element 36 is placed in proximity to interferometer reference resonator cavity loop 28c so as to tune the resonant frequency thereof. The second end of second optical waveguide 42 is connected to a first split input of second splitter 40, and the second end of third optical waveguide 44 is connected to a second split input of second splitter 40. The output of second splitter 40 is connected to one end of output optical waveguide 18.

In operation, sensing element 16" of FIG. 4c operates similarly to that of sensing element 16" of FIG. 4a with the notable exception of the use reference resonators 28e and 28f to create a narrow frequency filter in a manner similar to that described above in relation to FIG. 3b. An optical signal propagating in input optical waveguide 14 is coupled at the common resonant frequency of reference resonators 28e and 28f to first optical waveguide 22. Reference resonator 28e is shown to be of a different size than reference resonator 28f, thus with appropriate tuning, utilizing optional first and second tuning elements 36, a mutual common resonance can be found. In an exemplary embodiment the combination of reference resonator 28e and 28f exhibit only a single narrow common resonant frequency over the bandwidth of transmitter 12, and thus only a single narrow bandwidth is transferred to first optical waveguide 22. Transmitter 12 of FIG. 1 can therefore be a reduced cost broadband light source without impacting the sensitivity of sensing element 16". In another embodiment, optional first and second tuning elements are operated to sweep the common resonance frequency of reference resonators 28e and 28f over a range of frequencies, thus transmitter 12 can comprise a single low cost broadband source.

Figure 5A:
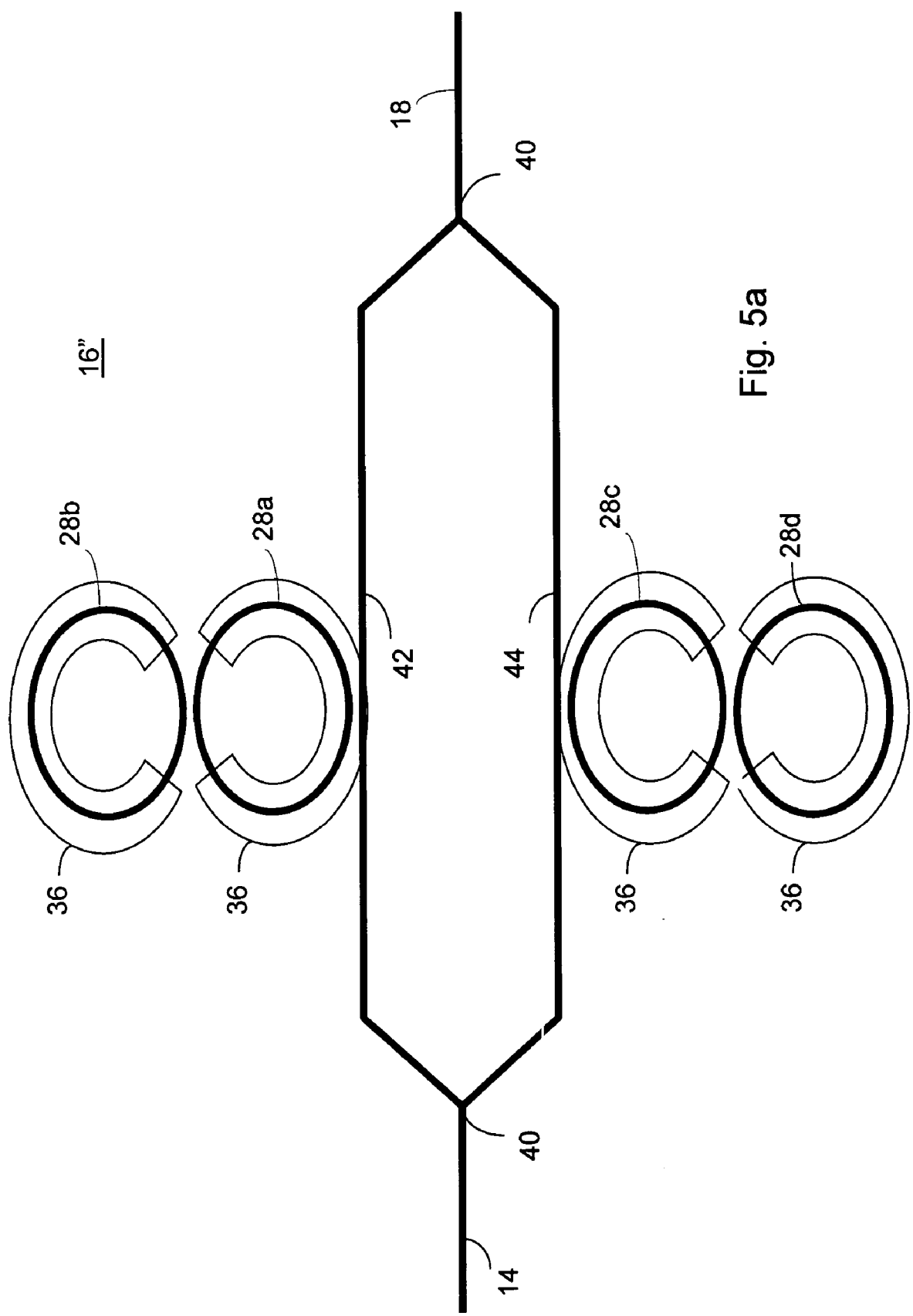
FIG. 5a illustrates a high level block diagram of a fourth embodiment of an interferometer based sensing element comprising a reference arm in accordance with the teaching of the invention.

FIG. 5a illustrates a high level block diagram of a fourth embodiment of an interferometer based sensing element 16" exhibiting enhanced sensitivity, comprising two sensing resonator cavity loop 28a and 28b and two interferometer reference resonator cavity loop 28c and 28d. Improved sensing element 16" is operable to replace sensing element 16 of FIG. 1 and to be operable as part of sensing system 10. Sensing element 16" comprises input optical waveguide 14, splitters 40, first optical waveguide 42, second optical waveguide 44, sensing resonator cavity loops 28a and 28b, interferometer reference resonator cavity loops 28c and 28d, optional tuning elements 36 and output optical waveguide 18. Input optical waveguide 14 is connected to the input of first splitter 40, and a first split output of first splitter 40 is connected to one end of first optical waveguide 42. Second split output of first splitter 40 is connected to one end of second optical waveguide 44. First optical waveguide 42 is placed in close proximity to at least a portion of first sensing resonator cavity loop 28a thus creating a first interaction area of evanescent coupling. Optional first tuning element 36 is placed in proximity to first sensing resonator cavity loop 28a so as to tune the resonant frequency thereof. Second sensing resonator cavity loop 28b is placed in close proximity to at least a portion of first sensing resonator cavity loop 28a thus creating a second interaction area of evanescent coupling. Optional second tuning element 36 is placed in proximity to second sensing resonator cavity loop 28b so as to tune the resonant frequency thereof. Second optical waveguide 44 is placed in close proximity to at least a portion of first interferometer reference resonator cavity loop 28c thus creating a third interaction area of evanescent coupling. Optional third tuning element 36 is placed in proximity to first interferometer reference resonator cavity loop 28c so as to tune the resonant frequency thereof. Second interferometer reference resonator cavity loop 28d is placed in close proximity to at least a portion of first interferometer reference resonator cavity loop 28c thus creating a fourth interaction area of evanescent coupling. Optional fourth tuning element 36 is placed in proximity to second interferometer reference resonator cavity loop 28d so as to tune the resonant frequency thereof. The second end of first optical waveguide 42 is connected to a first split input of second splitter 40, and the second end of second optical waveguide 44 is connected to a second split input of second splitter 40. The output of second splitter 40 is connected to one end of output optical waveguide 18.

In operation sensing element 16" of FIG. 5a operates in a manner similar to that of sensing element 16" of FIG. 4a with the added benefit of having a second sensing resonator cavity loop 28b to increase the sharpness of the Q or roll-off. It is to be understood that the use of second sensing resonator cavity loop 28b and second interferometer reference resonator cavity loop 28d is not meant to be limiting in any way, and three or more sensing resonator cavity loops may be utilized to increase the sensitivity further without exceeding the scope of the invention. A like number of interferometer reference resonator cavity loops are preferably supplied. The addition of further cascaded sensing resonator cavity loops increases the sensitivity following a power law function.

Sensing resonator cavity loops 28a and 28b are exposed to the environment or pressure source. In an exemplary embodiment this is accomplished by opening a window to allow sensing resonator cavity loop 28a and 28b to be in contact with the environment or pressure source. In another exemplary embodiment, sensing resonator cavity loops 28a and 28b are utilized to detect the presence or absence of a specific chemical by the deposition of a pre-determined reacting chemically active substance directly on sensing resonator cavity loops 28a and 28b. The pre-determined reacting chemically active substance is then made to be in contact with, or accessible to, the material or gas under test, preferably through an open window. The pre-determined reacting chemically active substance is chosen to change its optical behavior, and as a result the optical behavior of sensing resonator cavity loops 28a and 28b, in response to the presence or absence of the specific chemical.

FIG. 5b illustrates a high level block diagram of a fifth embodiment of an interferometer based sensing element 16" exhibiting enhanced sensitivity, comprising multiple sensing and reference resonator cavity loops in a drop waveguide configuration. Improved sensing element 16" is operable to replace sensing element 16 of FIG. 1 and to be operable as part of sensing system 10. Sensing element 16" comprises input optical waveguide 14, splitter 40, first optical waveguide 42, second optical waveguide 44, third optical waveguide 46, fourth optical waveguide 48, sensing resonator cavity loops 28a and 28b, interferometer reference resonator cavity loops 28c and 28d, optional tuning elements 36 and output optical waveguide 18. One end of input optical waveguide 14 is connected to the input of first splitter 40, and a first split output of first splitter 40 is connected to one end of first optical waveguide 42. Second split output of first splitter 40 is connected to one end of second optical waveguide 44. First optical waveguide 42 is placed in close proximity to at least a portion of first sensing resonator cavity loop 28a thus creating a first interaction area of evanescent coupling. Optional first tuning element 36 is placed in proximity to first sensing resonator cavity loop 28a so as to tune the resonant frequency thereof. Second sensing resonator cavity loop 28b is placed in close proximity to at least a portion of first sensing resonator cavity loop 28a thus creating a second interaction area of evanescent coupling. Optional second tuning element 36 is placed in proximity to second sensing resonator cavity loop 28b so as to tune the resonant frequency thereof. Second optical waveguide 44 is placed in close proximity to at least a portion of first interferometer reference resonator cavity loop 28c thus creating a third interaction area of evanescent coupling. Optional third tuning element 36 is placed in proximity to first interferometer reference resonator cavity loop 28c so as to tune the resonant frequency thereof. Second interferometer reference resonator cavity loop 28d is placed in close proximity to at least a portion of first interferometer reference resonator cavity loop 28c thus creating a fourth interaction area of evanescent coupling. Optional fourth tuning element 36 is placed in proximity to second interferometer reference resonator cavity loop 28d so as to tune the resonant frequency thereof. Third optical waveguide 46 is placed in close proximity to at least a portion of second interferometer reference resonator cavity loop 28d thus creating a fifth interaction area of evanescent coupling. Fourth optical waveguide 48 is placed in close proximity to at least a portion of second sensing resonator cavity loop 28b thus creating a sixth interaction area of evanescent coupling. One end of third optical waveguide 46 is connected to a first split input of second splitter 40, and one end of fourth optical waveguide 48 is connected to a second split input of second splitter 40. The output of second splitter 40 is connected to one end of output optical waveguide 18.

In operation, sensing element 16" of FIG. 5b operates similarly to that of sensing element 16" of FIG. 5a with the notable exception that the drop waveguides 46 and 48 are utilized. Advantageously, only energy at the common resonant frequency of sensing resonator cavity loops 28a, 28b and interferometer reference cavity loops 28c, 28d, respectively, appear at output waveguide 18 and are received by detector 20. Transmitter 12 of FIG. 1 can therefore be a reduced cost broadband light source without impacting the sensitivity of sensing element 16".

Optical gyroscopes that make use of the group delay dependence on the relative velocity between light and matter by employing Sagnac interferometry are also improved by one aspect of the invention. Optical gyroscopes are known in the art, and in one embodiment comprise an optical resonator as described in U.S. Pat. No. 5,327,215 issued to Bernard et al whose contents are incorporated herein by reference.

FIG. 6 illustrates a high level block diagram of a first embodiment of an improved optical gyroscope sensor 50 comprising transmitter 12, input optical waveguides 14a and 14b, splitter 40, detector 20, unattached end 54, four port splitter 52, first optical waveguide 42, second optical waveguide 44, first sensing resonator cavity loop 28a, second sensing resonator cavity loop 28b and transfer resonator cavity loop 28g. Transmitter 12 is connected to one end of input optical waveguide 14a, and the second end of input optical waveguide 14a is connected to one port of splitter 40, which acts as an input port. A second port of splitter 40 that acts as an output port is connected to detector 20, and the third port of splitter 40 is connected to one end of input optical waveguide 14b. The third port of splitter 40 acts as both an input and output port in a manner to be described further herein to below. The second end of input optical waveguide 14b is connected to one port of four port splitter 52, which acts in a bi-directional manner. A second port of four port splitter 52 acts as an output port and is left open at sump connection 54. A third port of four port splitter 52, which acts as a bi-directional port is connected to one end of first optical waveguide 42, and the fourth port of four port splitter 52, which acts as a bi-directional port is connected to one end of second optical waveguide 44. First optical waveguide 42 and second optical waveguide 44 are each placed in close proximity to at least a portion first sensing resonator cavity loop 28a thus creating a first and second interaction area of evanescent coupling. Transfer cavity loop 28g is placed within both first sensing resonator cavity loop 28a and second sensing resonator cavity loop 28b so as to create an interaction area with first sensing resonator cavity loop 28a and a separate interaction area with second sensing resonator cavity loop 28b. Tuning elements (not shown) may be further placed in proximity to first and second sensing resonator cavity loop 28a and 28b as required to establish a common resonant frequency of the sensing and transfer resonator cavity loops.

In operation light exiting transmitter 12 propagates through input optical waveguides 14a and 14b and enters first optical waveguide 42. Light propagating in first optical waveguide 42 propagates in a clockwise direction in first sensing resonator cavity loop 28a, and is transferred clockwise into transfer cavity loop 28g, and continues to propagate in a clockwise direction in second resonator cavity loop 28b. Light at or near the resonant condition will further propagate in second optical waveguide 44 in the direction of four-port coupler 52, a portion of which energy will be detected by detector 20. Similarly light exiting transmitter 12 propagates through input optical waveguide 14a and 14b and enters second optical waveguide 44. Light propagating in second optical waveguide 44 propagates in a counter-clockwise direction through sensing resonator cavity loops 28a, 28b and transfer resonator cavity loop 28g. Light at the resonant condition will further propagate in first optical waveguide 42 in the direction of four-port coupler 52, a portion of which energy will be detected by detector 20. At rest the propagation paths comprising the clockwise and counterclockwise directions of sensing resonator cavity loops 28a and 28b are nearly identical, and thus the two signals are in phase and interfere with each other constructively at detector 20. Any minor differences in phase can be resolved by a combination of appropriate calibration means (not shown), adjustment of the wavelength of transmitter 12 or by electronic processing of the signal received from detector 20.

Motion of sensing optical resonator cavity loops 28a and 28b in the plane of the resonator cavity loops 28a, 28b will create a phase difference detected in the Sagnac-type interferometer, which is sensitive to the optical path difference between the clockwise and counter-clockwise paths for sensing resonator cavity loop 28a, 28b and transfer resonator cavity loop 28g. The optical path difference will manifest itself in a difference in phase between the two signals being detected at detector 20, and the amount of interference is a function of the motion within the plane of sensing resonator cavity loops 28a, 28b and transfer resonator cavity loop 28g. Motion within the plane is thus the parameter that is measured by optical gyroscope sensor 50.

FIG. 7 illustrates a high level block diagram of a second embodiment of an improved optical gyroscope sensor 60, which is in all respects similar to that optical gyroscope sensor 50 of FIG. 6 with the notable exception that second sensing resonator cavity loop 28b is placed within the boundaries of first resonator cavity loop 28a, and thus transfer resonator cavity loop 28g is not required. Second sensing resonator cavity loop 28b is smaller than first sensing resonator cavity loop 28a, and is preferably designed such that the resonance conditions of both first and second sensing resonator cavity loop 28a and 28b exhibit a mutual common resonance at a specific wavelength. Second sensing resonator cavity loop 28b is placed in proximity to a portion of first sensing resonator cavity loop 28a, thus creating a single interaction area of evanescent coupling, and maintaining the unity of a clockwise or counter-clockwise propagation direction.

FIG. 8 illustrates a high level block diagram of a third embodiment of an improved optical gyroscope sensor 62, which is in all respects similar to that of optical gyroscope sensor 50 of FIG. 6 with the notable exception that second sensing resonator cavity loop 28b is placed within the boundaries of first sensing resonator cavity loop 28a, and exhibits two interaction areas of evanescent coupling 56 between first sensing resonator cavity loop 28a and second sensing resonator cavity loop 28b. The two interaction areas of evanescent coupling 56 enable added design flexibility in the phase difference between the coupling areas, while maintaining the unity of a clockwise or counter-clockwise propagation direction. Tuning elements (not shown) may be further placed in proximity to first and second sensing resonator cavity loop 28a and 28b as required to establish a common resonant frequency of the sensing and transfer resonator cavity loops.

FIG. 9 illustrates a high level block diagram of a third embodiment of an improved optical gyroscope sensor 64, which is in all respects similar to that optical gyroscope sensor 50 of FIG. 6 with the notable exception that second sensing resonator cavity loop 28*b* is spaced apart from first sensing resonator cavity loop 28*a* by spacer 66. There is thus no direct interaction between first sensing resonator cavity loop 28*a* and second sensing resonator cavity loop 28*b*. First sensing resonator cavity loop 28*a* interacts with first optical waveguide 42, and second sensing resonator cavity loop 28*b* interacts with first optical waveguide 42. First sensing resonator cavity loop 28*a* interacts with second optical waveguide 44, and second sensing resonator cavity loop 28*b* interacts with second optical waveguide 44. The operation of first and second resonator cavity loops 28*a* and 28*b* are independent, and the filtering effect is additive, creating a sharp Q function. Operating optical gyroscope sensor 64 at or near resonance will result in a sensitive sensor. Optical gyroscope sensor 64 exhibits the additional benefit of having an overall larger cavity length, thus increasing the response for a given angular motion. Tuning elements (not shown) may be further placed in proximity to first and second sensing resonator cavity loop 28*a* and 28*b* as required to establish a common resonant frequency of the sensing and transfer resonator cavity loops.

Thus the present invention provides a method and apparatus for optical sensing which provides a highly sensitive output signal representative of a sensed parameter that is adaptable to a large variety of sensing applications. The present invention utilizes multiple resonator cavity loops, which in combination exhibit sharp roll off when the resonance condition is not met, and thus enable a highly sensitive output signal representative of the sensed parameter.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

We claim:

1. An optical sensor system for providing an output signal in response to a sensed parameter comprising:
    an optical signal source for generating an input optical signal;
    a reference arm;
    a sensing element in optical communication with said optical signal source, said sensing element comprising at least two resonant cavity loops exhibiting a common resonant frequency near at least one frequency of said input optical signal, at least one of said resonant cavity loops being exposed to an external parameter, said external parameter modifying the resonant frequency of said at least one exposed resonant cavity loop thereby modifying an optical output signal; and
    a detector in optical communication with said sensing element, said detector detecting any modification in said output optical signal in response to the sensed parameter,
    one of said resonator cavity loops being an interferometer reference resonator cavity loop disposed on said reference arm, said at least one resonant cavity loop exposed to an external parameter defining the measurement arm of said interferometer.

2. An optical sensor system according to claim 1, further comprising drop waveguides for each of said reference resonator cavity loop and said exposed resonator cavity loop.

3. An optical sensor system according to claim 1, further comprising a reference resonant cavity loop, said reference resonant cavity loop filtering said optical signal source prior to being input to said interferometer reference resonator cavity loop and said exposed resonator cavity loop.

4. An optical sensor system according to claim 3, further comprising a tuning element operable to set the resonant frequency of said reference resonant cavity loop.

5. An optical sensor system according to claim 1, wherein said measurement arm of said interferometer comprises at least two resonant cavity loops exposed to said external parameter, said external parameter modifying the resonant frequency of said exposed at least two resonant cavity loops.

6. An optical sensor system according to claim 5, further comprising at least two interferometer reference resonator cavity loops.

7. An optical sensor system according to claim 6, wherein the number of said exposed resonator cavity loops is equal to the number of interferometer reference resonator cavity loops.

8. An optical sensor system for providing an output signal in response to a sensed parameter comprising:
    an optical signal source for generating an input optical signal;
    a sensing element in optical communication with said optical signal source, said sensing element comprising at least two resonant cavity loops exhibiting a common resonant frequency near at least one frequency of said input optical signal, at least one of said resonant cavity loops being exposed to an external parameter, said external parameter modifying the resonant frequency of said at least one exposed resonant cavity loop thereby modifying an optical output signal, wherein said external parameter is motion within the plane of said exposed at least one resonant cavity loop; and
    a detector in optical communication with said sensing element, said detector detecting any modification in said output optical signal in response to the sensed parameter,
    wherein said at least two resonant cavity loops are separated by a spacer, whereby no area of direct interaction is formed between said at least two resonant cavity loops.

9. An optical sensor system for providing an output signal in response to a sensed parameter comprising:
- an optical signal source for generating an input optical signal;
- a sensing element in optical communication with said optical signal source, said sensing element comprising at least two resonant cavity loops exhibiting a common resonant frequency near at least one frequency of said input optical signal, at least one of said resonant cavity loops being exposed to an external parameter, said external parameter modifying the resonant frequency of said at least one exposed resonant cavity loop thereby modifying an optical output signal, wherein said external parameter is motion within the plane of said exposed at least one resonant cavity loop;
- a detector in optical communication with said sensing element, said detector detecting any modification in said output optical signal in response to the sensed parameter; and
- a transfer resonant cavity loop forming an area of interaction with each of said at least two resonant cavity loops.

* * * * *